United States Patent
Ouriel et al.

(10) Patent No.: US 7,014,653 B2
(45) Date of Patent: Mar. 21, 2006

(54) FURCATED ENDOVASCULAR PROSTHESIS

(75) Inventors: Kenneth Ouriel, Pepper Pike, OH (US); Daniel G. Clair, Shaker Heights, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/028,113

(22) Filed: Dec. 20, 2001

(65) Prior Publication Data

US 2003/0120333 A1    Jun. 26, 2003

(51) Int. Cl.
   *A61F 2/06*    (2006.01)
(52) U.S. Cl. .................................. 623/1.14; 623/1.35
(58) Field of Classification Search ............... 623/1.13, 623/1.14, 1.32, 1.35, 1.36
   See application file for complete search history.

(56) References Cited

U.S. PATENT DOCUMENTS

| | | | |
|---|---|---|---|
| 4,617,932 A | 10/1986 | Kornberg | |
| 5,211,658 A | 5/1993 | Clouse | |
| 5,489,295 A | 2/1996 | Piplani et al. | |
| 5,527,355 A | 6/1996 | Ahn | |
| 5,562,724 A | 10/1996 | Vorwerk et al. | |
| 5,562,728 A | 10/1996 | Lazarus et al. | |
| 5,632,772 A * | 5/1997 | Alcime et al. | 623/1.35 |
| 5,693,083 A | 12/1997 | Baker et al. | |
| 5,693,088 A | 12/1997 | Lazarus | |
| 5,749,921 A | 5/1998 | Lenker et al. | |
| 5,755,778 A | 5/1998 | Kleshinski | |
| 5,824,036 A | 10/1998 | Lauterjung | |
| 5,843,170 A | 12/1998 | Ahn | |
| 5,851,228 A * | 12/1998 | Pinheiro | 623/1 |
| 5,855,601 A | 1/1999 | Bessler et al. | |
| 5,906,640 A | 5/1999 | Penn et al. | |
| 5,944,750 A | 8/1999 | Tanner et al. | |
| 5,961,546 A * | 10/1999 | Robinson et al. | 623/1 |
| 5,967,986 A | 10/1999 | Cimochowski et al. | |
| 5,968,090 A | 10/1999 | Ratcliff et al. | |
| 5,984,955 A | 11/1999 | Wisselink | |

(Continued)

OTHER PUBLICATIONS

Chuter et al. An Endovascular System for Thoracoabdominal Aortic Aneurysm Repair. *J. Endovascular Therapy*, 2001; 8:25-33.

(Continued)

*Primary Examiner*—Michael Thaler
(74) *Attorney, Agent, or Firm*—Tarolli, Sundheim, Covell & Tummino L.L.P.

(57) ABSTRACT

An endovascular prosthesis (10) includes a first end (16) a furcated second end (18), and an anchoring means (20). The first end has a longitudinally extending central lumen (32) and means (40) for laterally supporting the first end. The furcated second end (18) includes at least two branches (64) that extend from an intersection of the furcated second end. Each of the branches (64) includes a longitudinal support means (84) and a branch lumen (78) in fluid communication with the central lumen (32) of the first end (16). The anchoring means (20) secures the first end (18) within a vasculature.

10 Claims, 18 Drawing Sheets

U.S. PATENT DOCUMENTS

| | | | |
|---|---|---|---|
| 6,004,348 A | 12/1999 | Banas et al. | |
| 6,036,723 A * | 3/2000 | Anidjar et al. | 623/1 |
| 6,051,020 A | 4/2000 | Goicoechea et al. | |
| 6,090,133 A | 7/2000 | Richter et al. | |
| 6,099,548 A | 8/2000 | Taheri | |
| 6,099,558 A * | 8/2000 | White et al. | 623/1.16 |
| 6,102,938 A * | 8/2000 | Evans et al. | 623/1.35 |
| 6,136,022 A | 10/2000 | Nunez et al. | |
| 6,159,565 A | 12/2000 | Campbell et al. | |
| 6,183,504 B1 | 2/2001 | Inoue | |
| 6,319,278 B1 * | 11/2001 | Quinn | 623/1.13 |
| 6,334,869 B1 * | 1/2002 | Leonhardt et al. | 623/1.13 |
| 6,361,556 B1 | 3/2002 | Chuter | |
| 6,814,752 B1 * | 11/2004 | Chuter | 623/1.35 |
| 2002/0019665 A1 * | 2/2002 | Dehdashtian et al. | 623/1.35 |
| 2002/0198587 A1 * | 12/2002 | Greenberg et al. | 623/1.13 |
| 2003/0065378 A1 * | 4/2003 | Chevillon et al. | 623/1.13 |

OTHER PUBLICATIONS

Blum, Ulrich. The MinTec System. In: Hopkinson et al. *Endovascular Surgery for Aortic Aneurysms*. London: WB Saunders, 1997, 6:72-87.

Chuter. Chuter-Gianturco Bifurcated Stent-Grafts for Abdominal Aortic Aneurysm Exclusion. In: Hopkinson et al. *Endovascular Surgey for Aortic Aneurysms*. London: WB Saunders, 1997, 7:88-103.

* cited by examiner

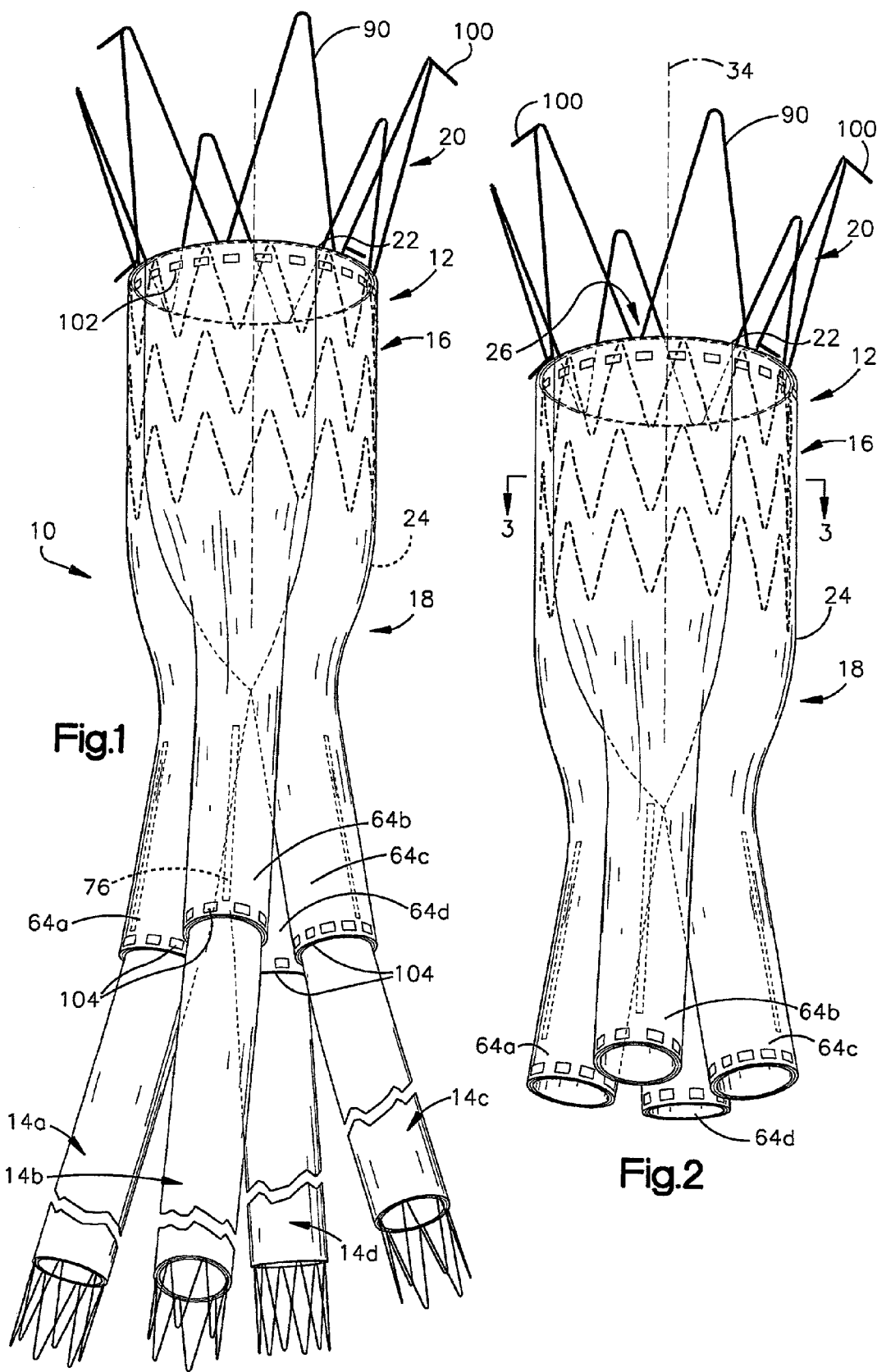

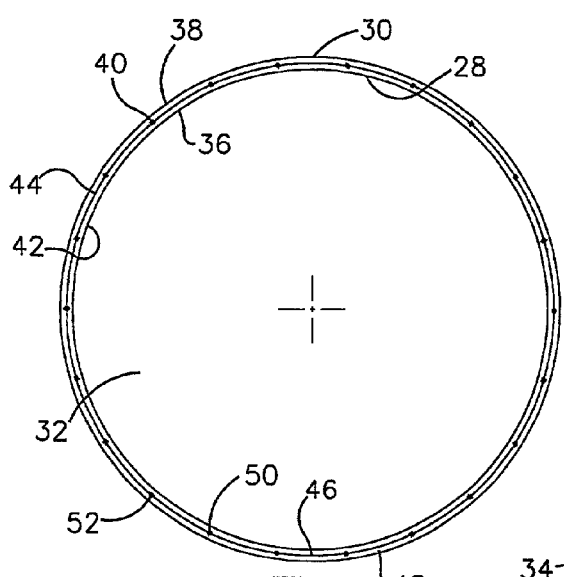
Fig.3
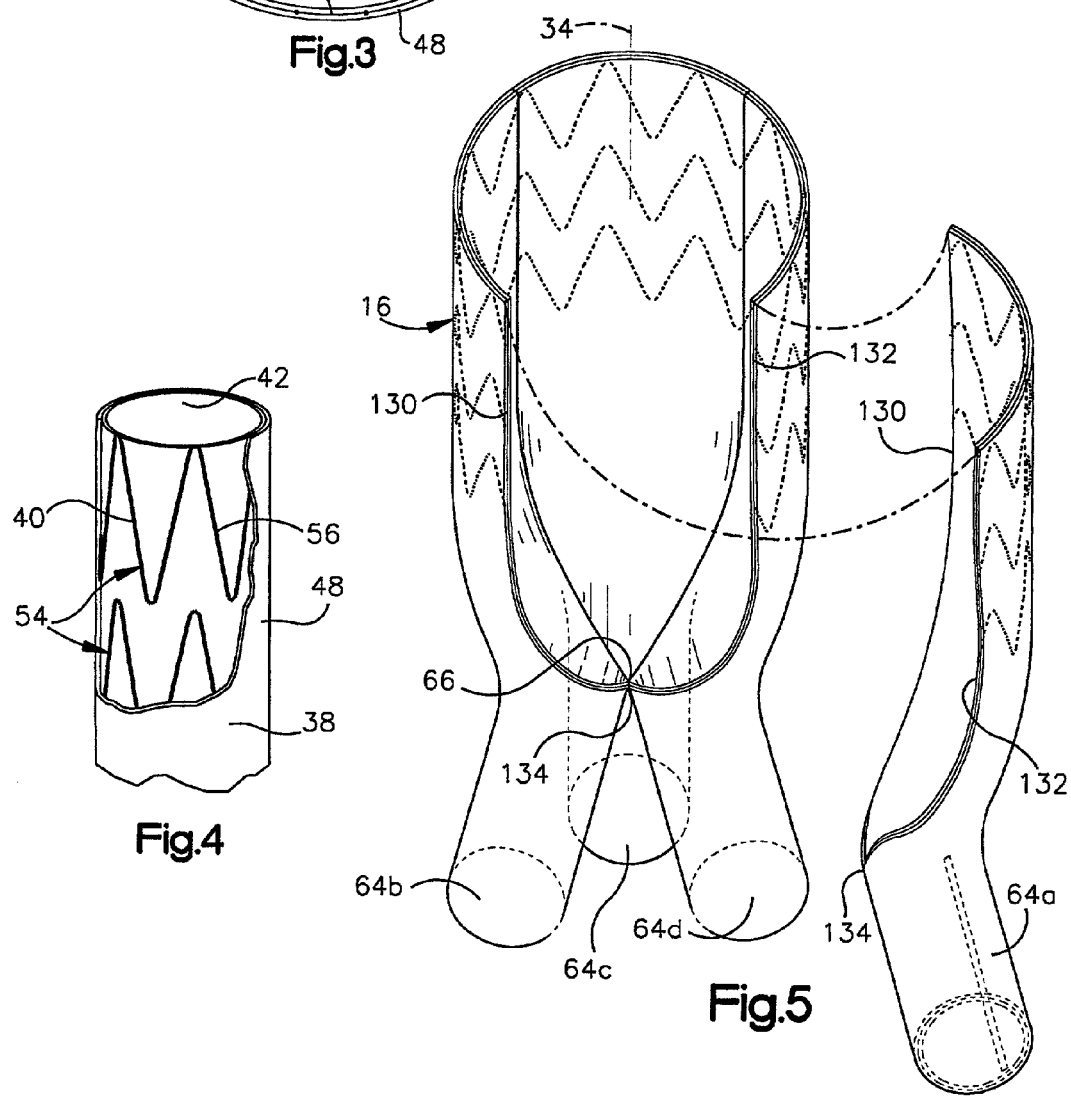
Fig.4
Fig.5

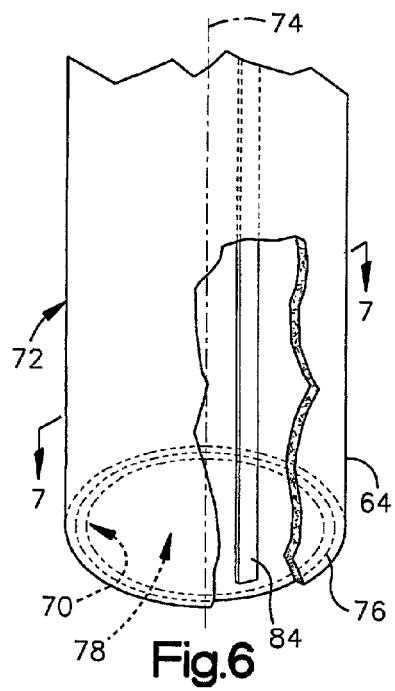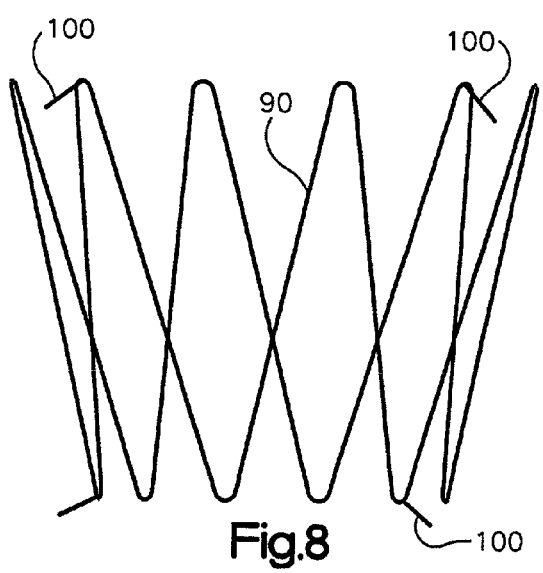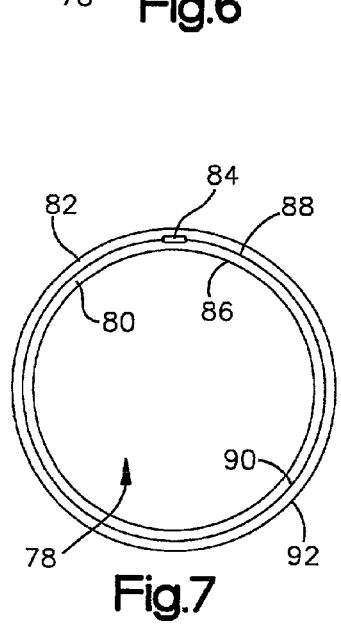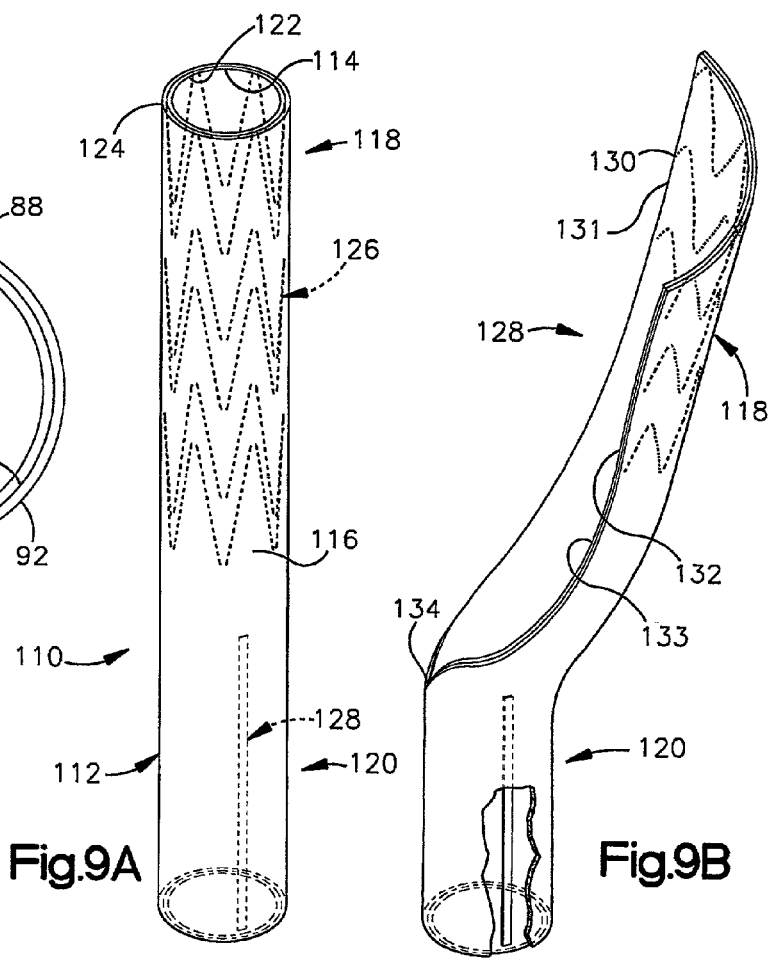

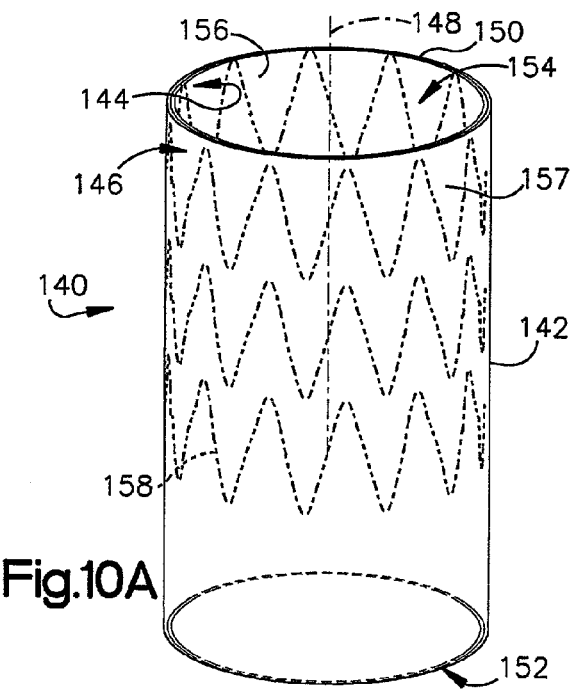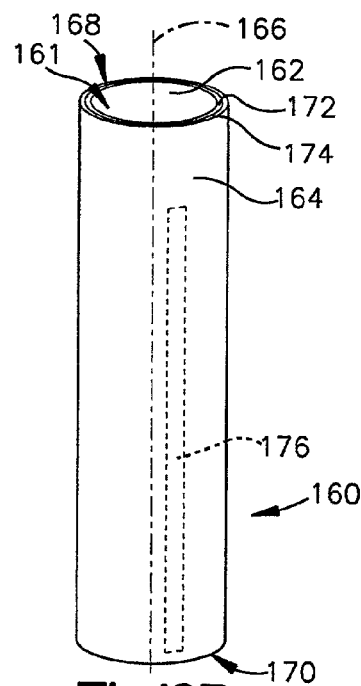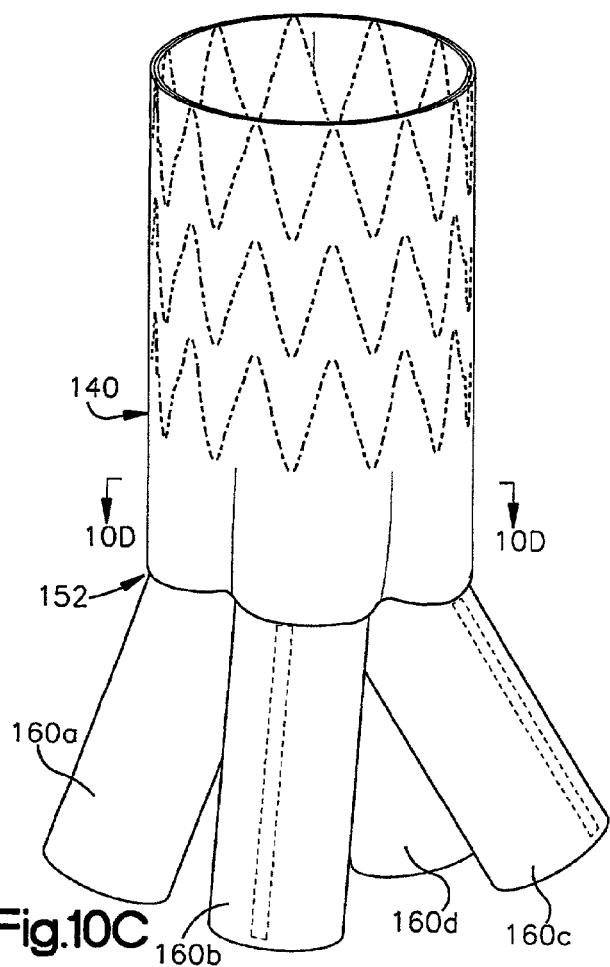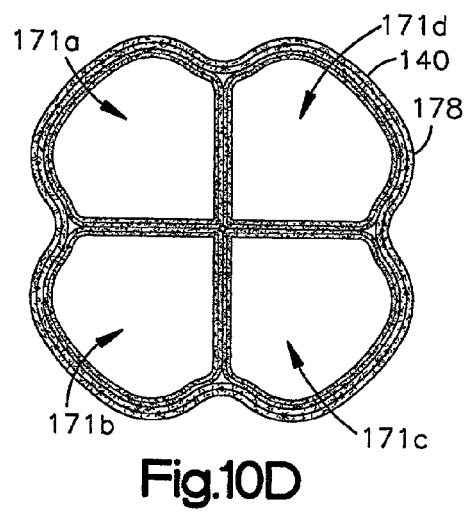

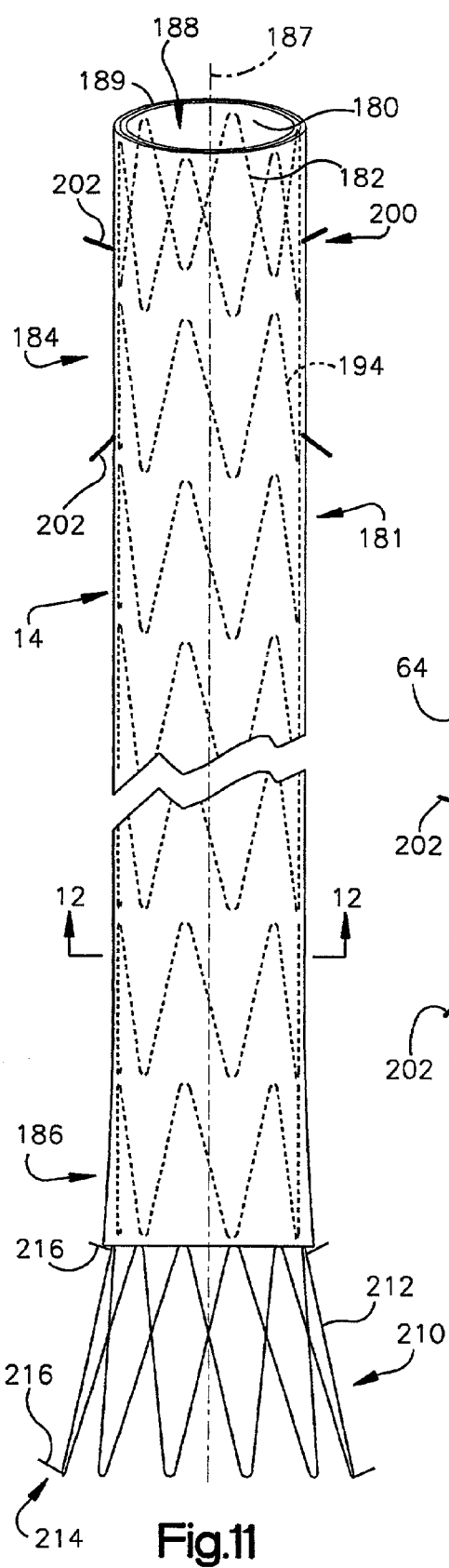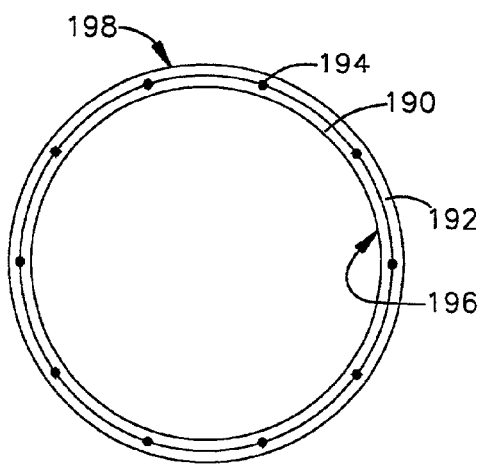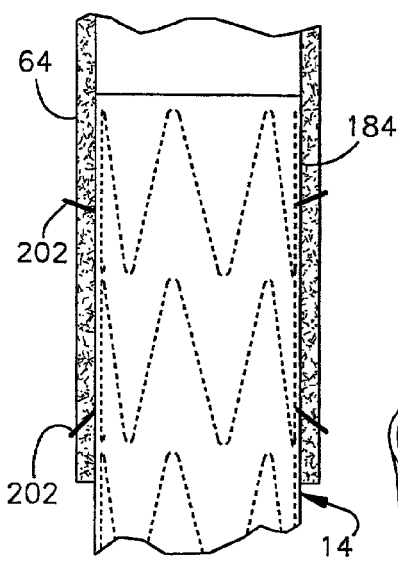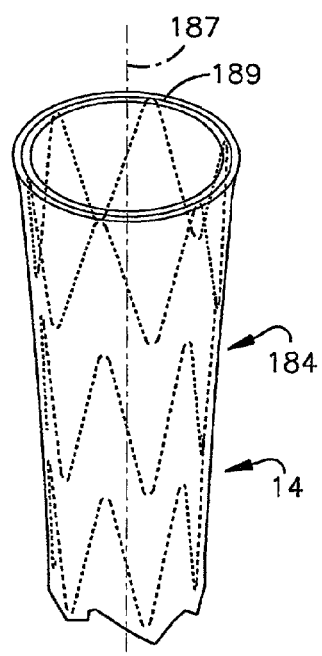
Fig. 11
Fig. 12
Fig. 13
Fig. 14

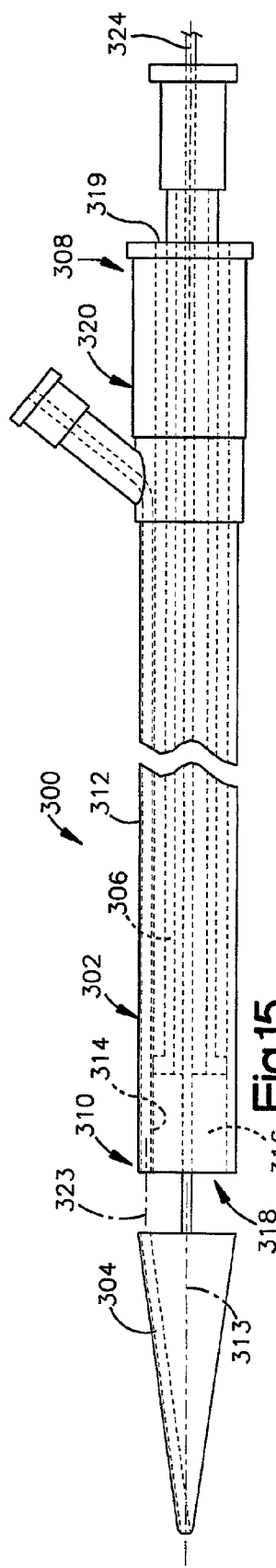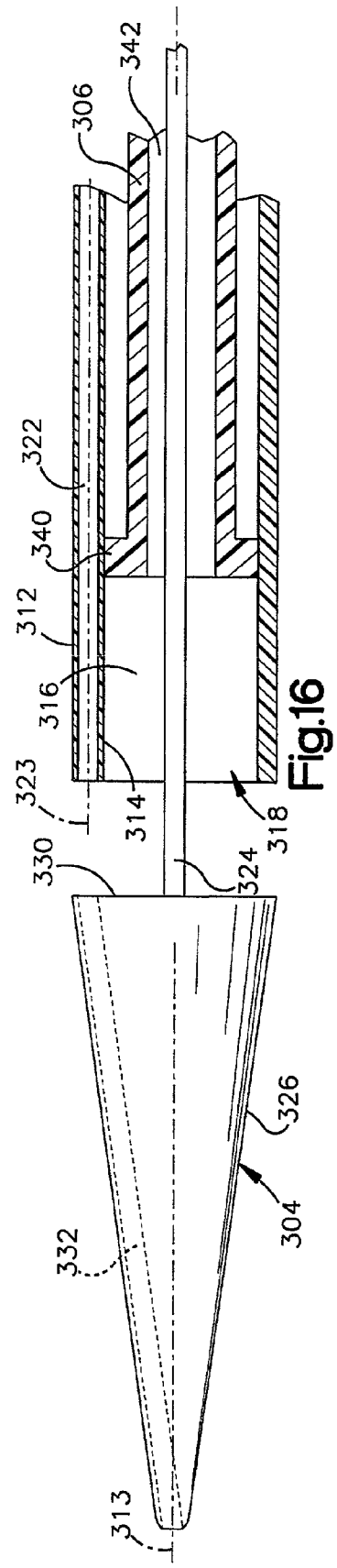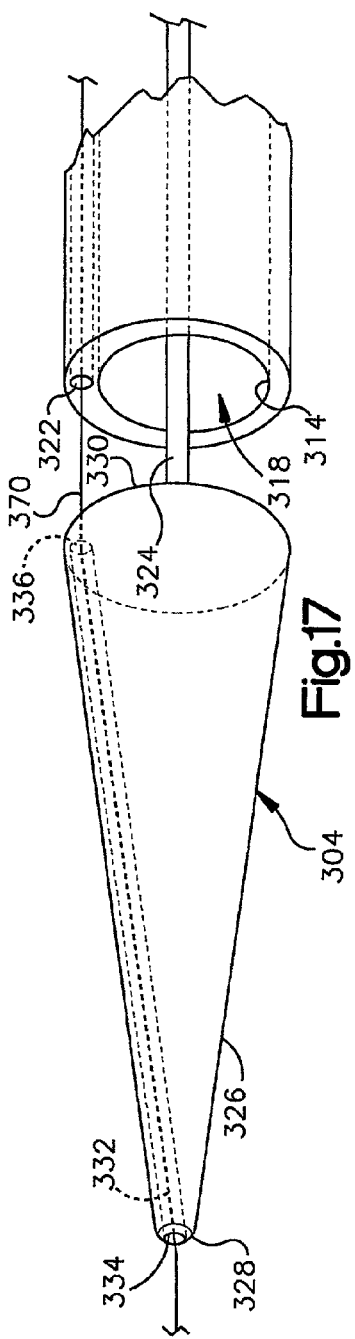

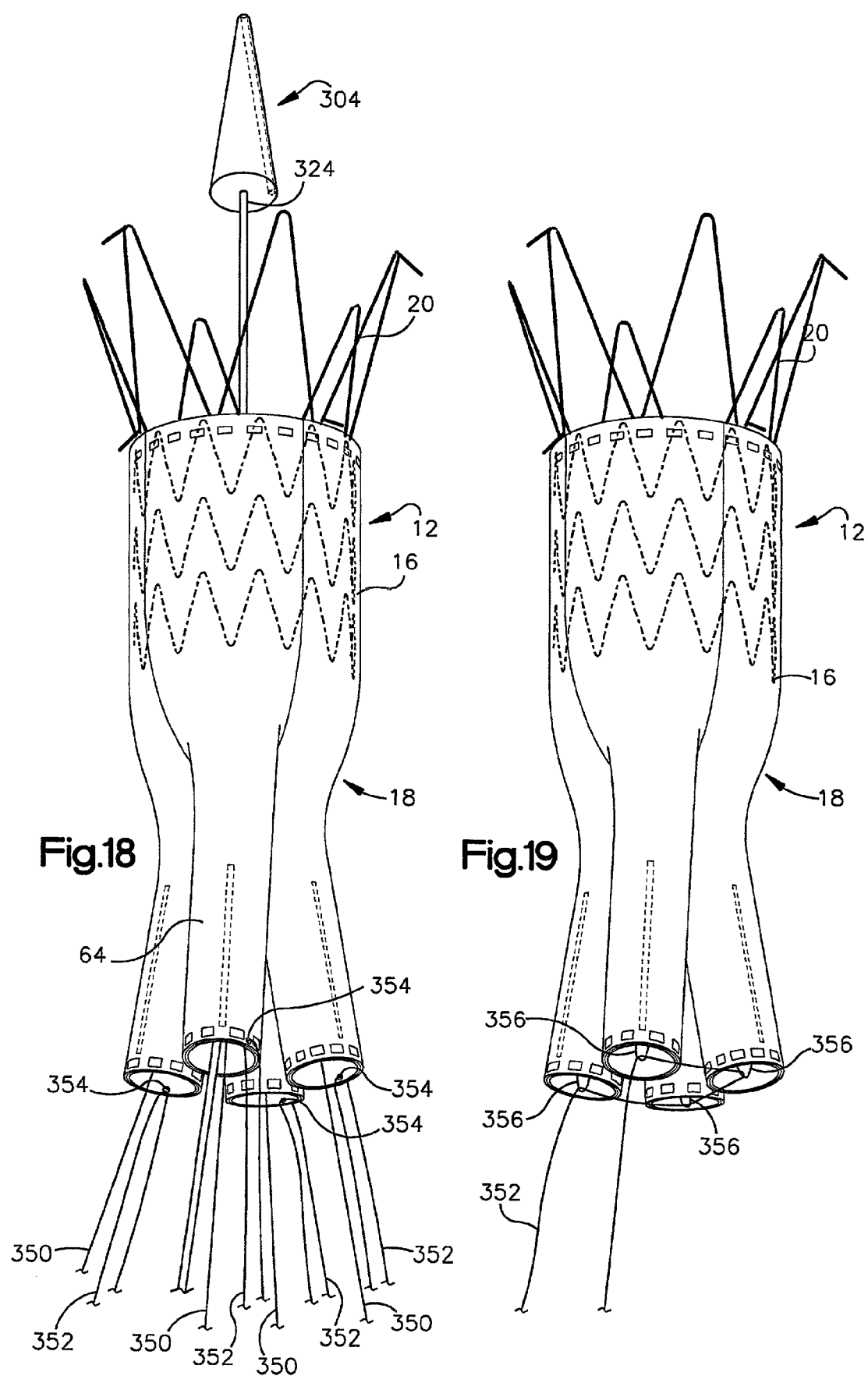

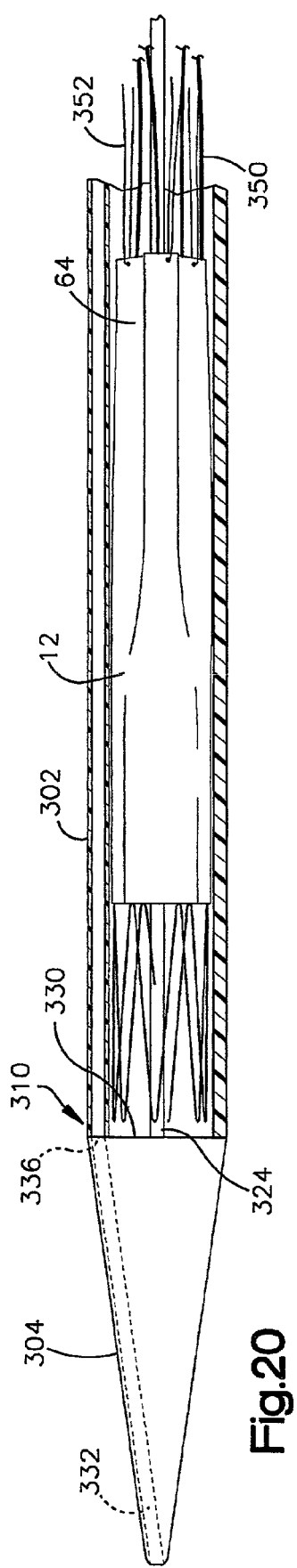
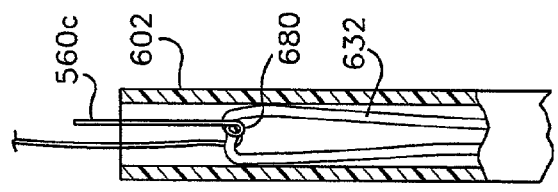
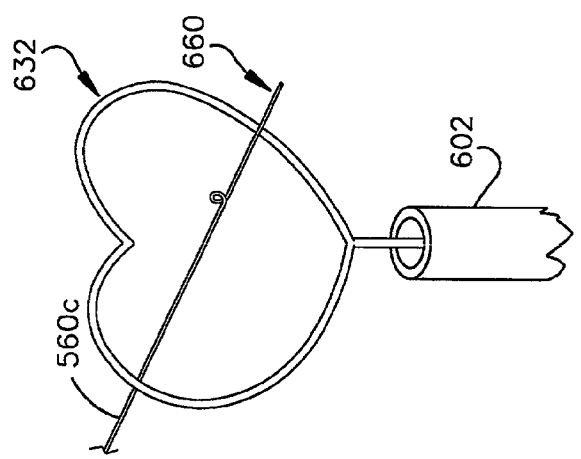
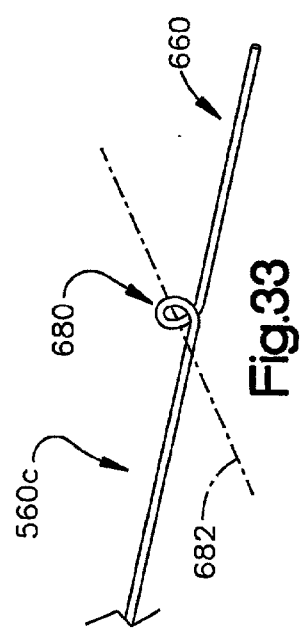

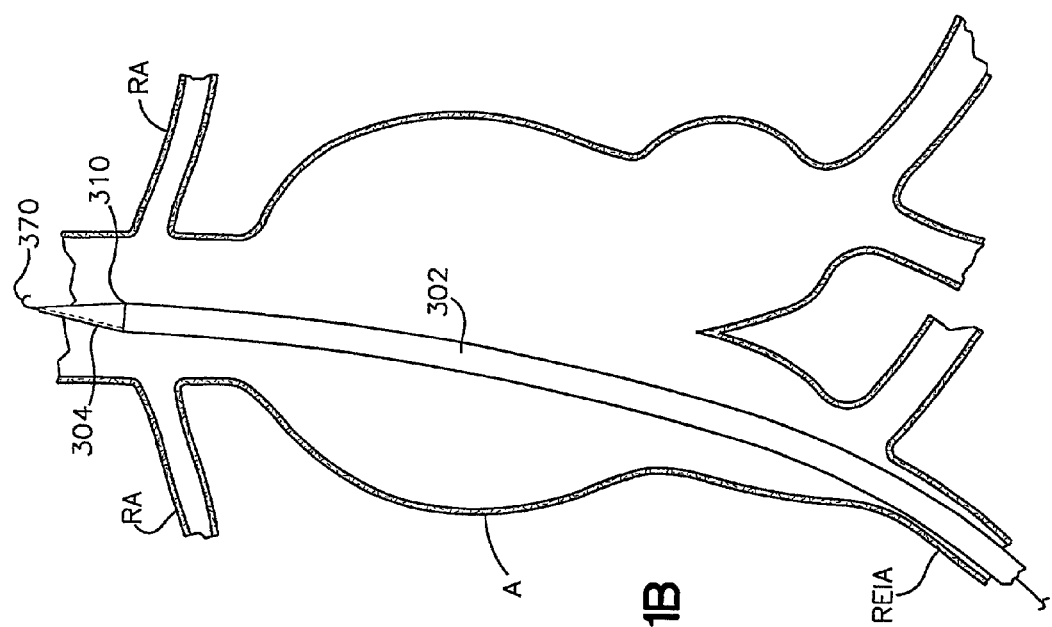
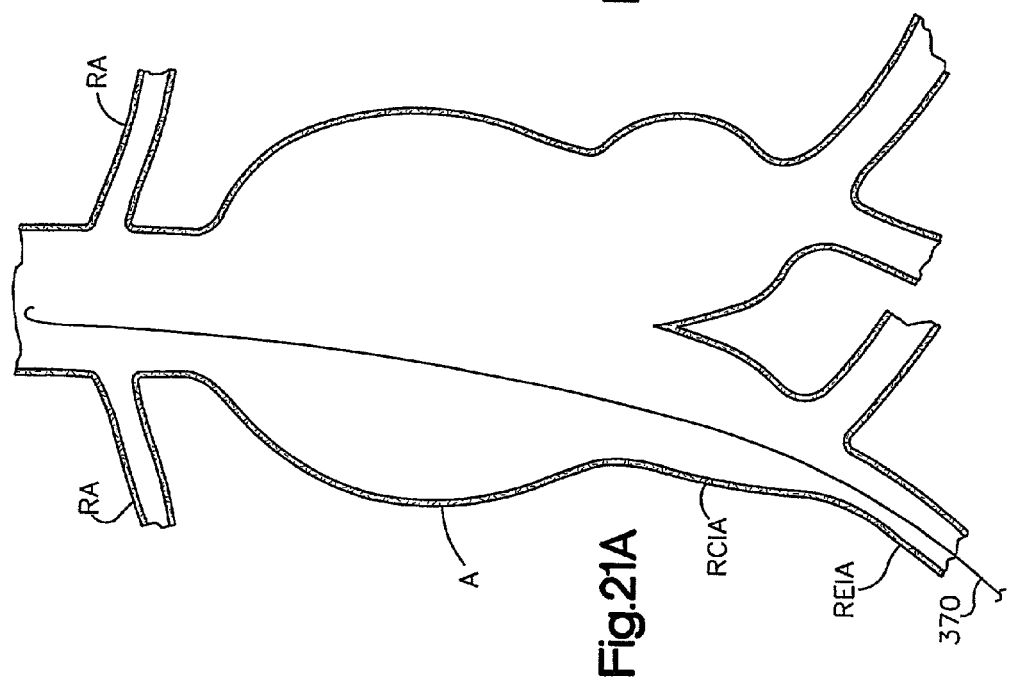

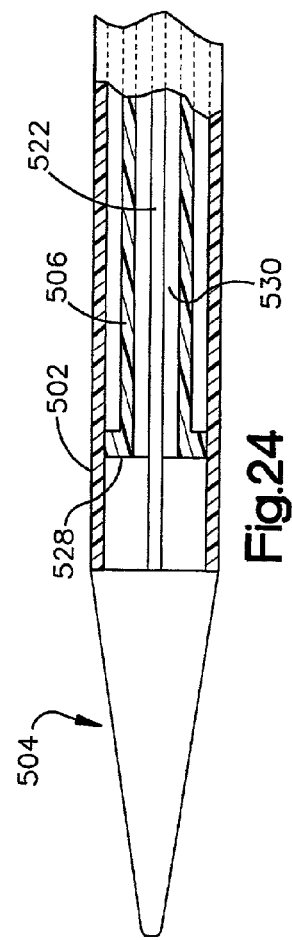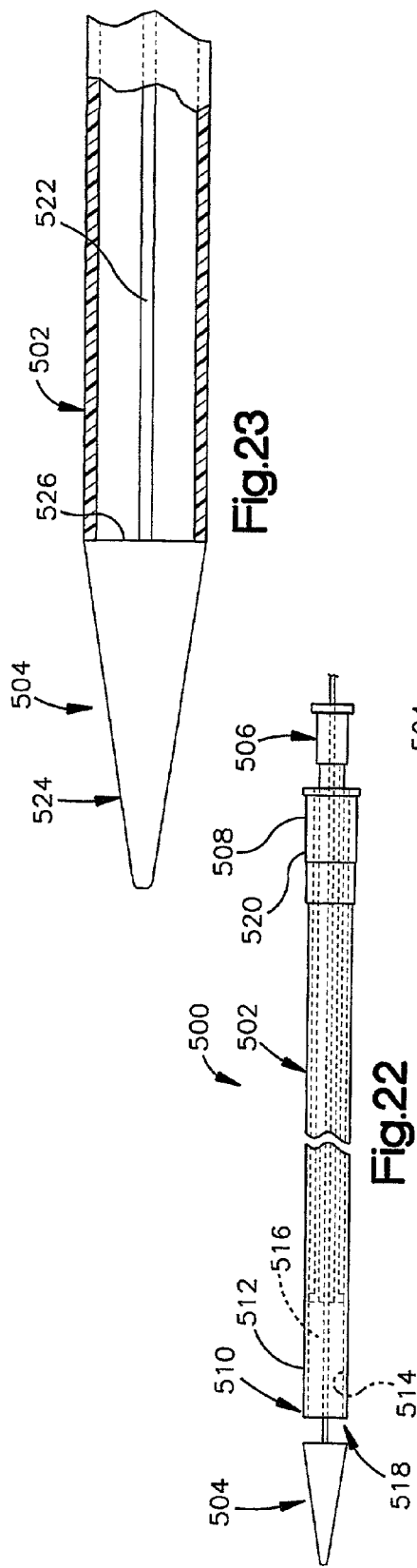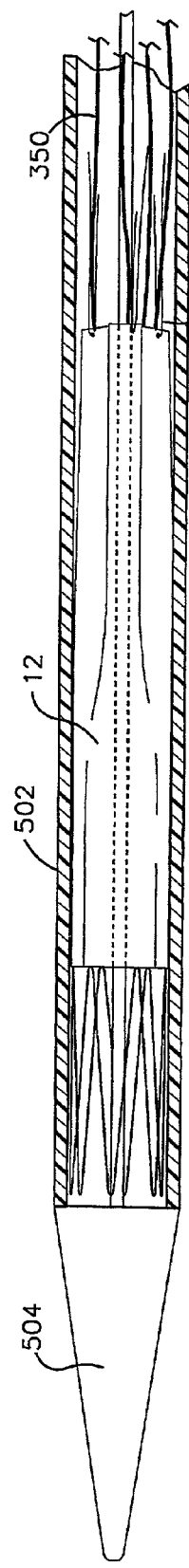

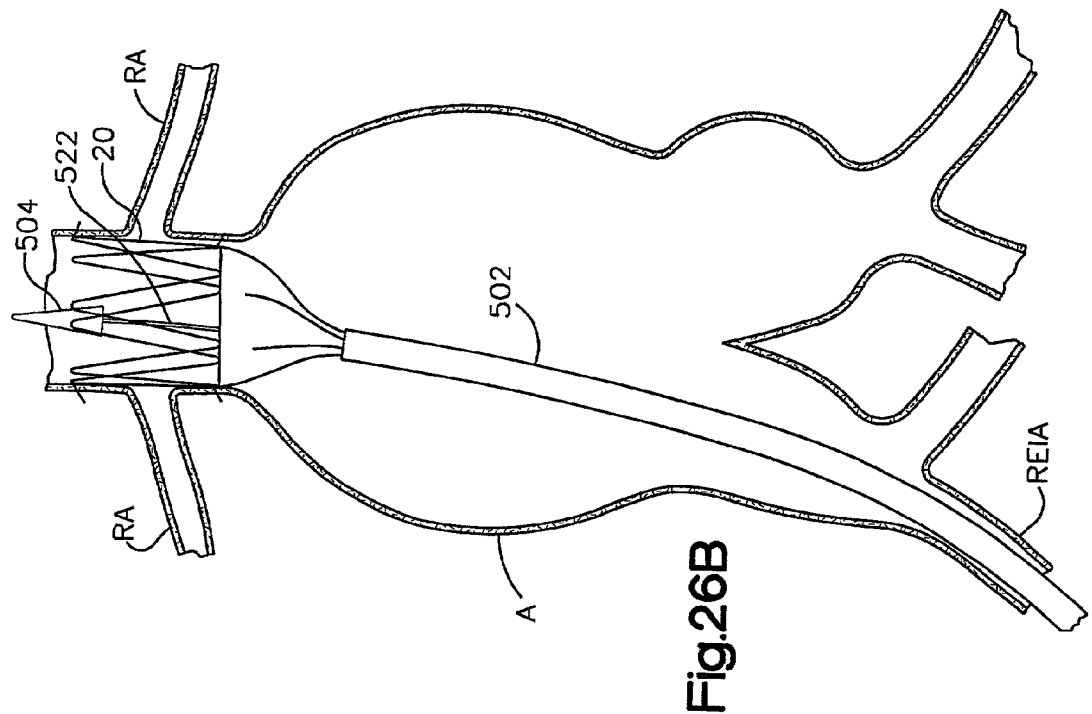
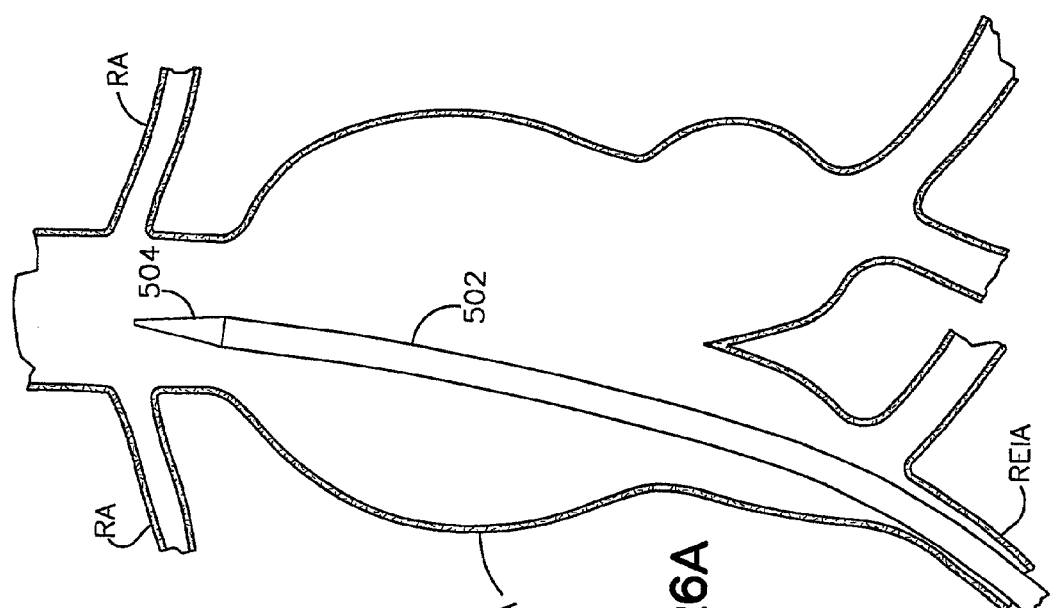

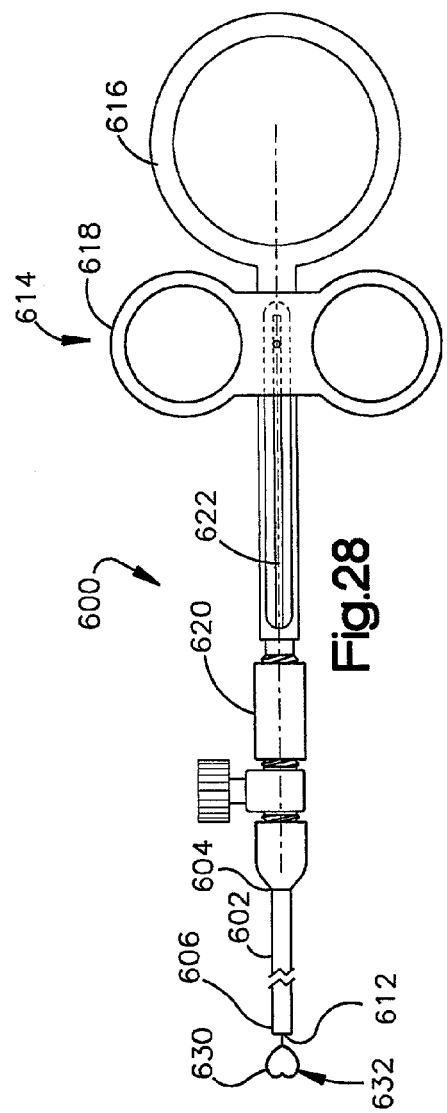
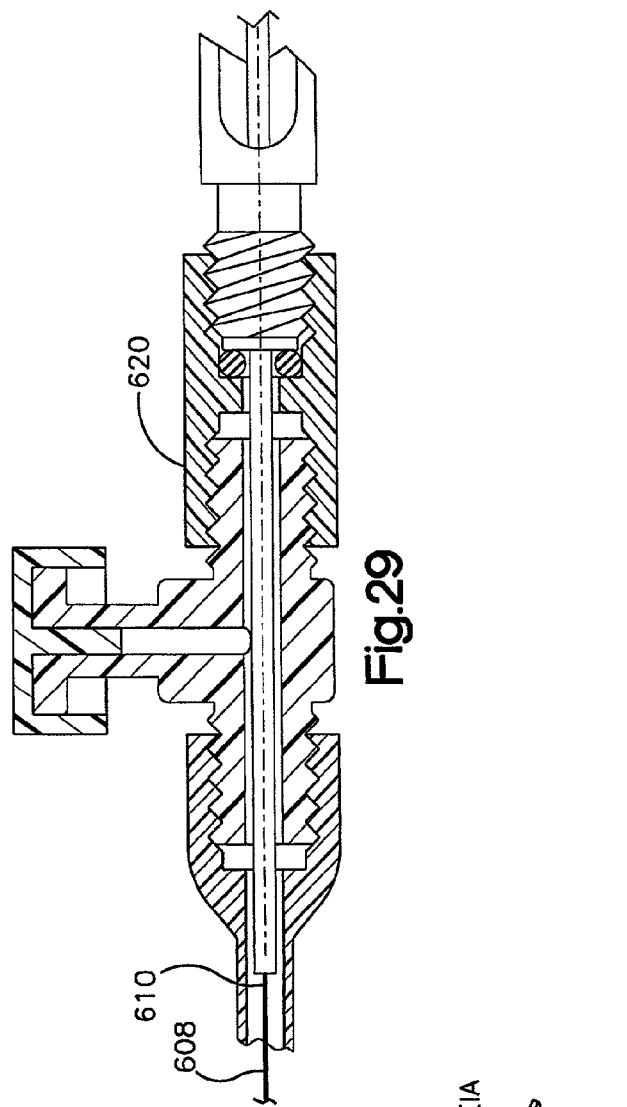
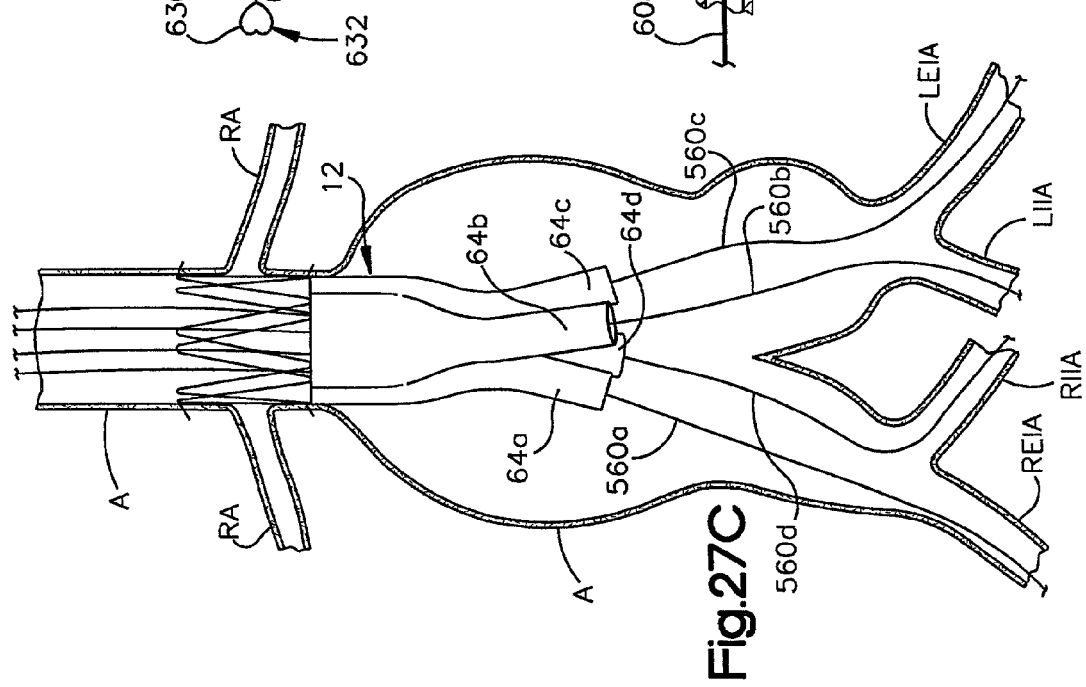

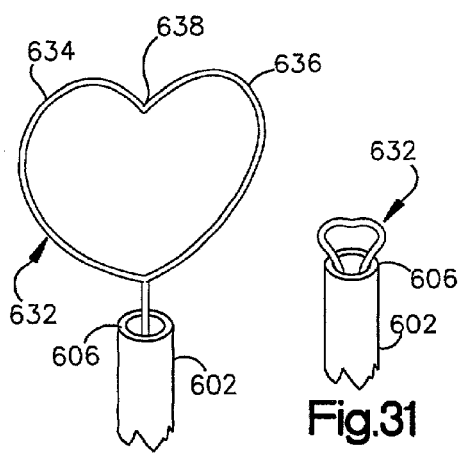
Fig.30
Fig.31
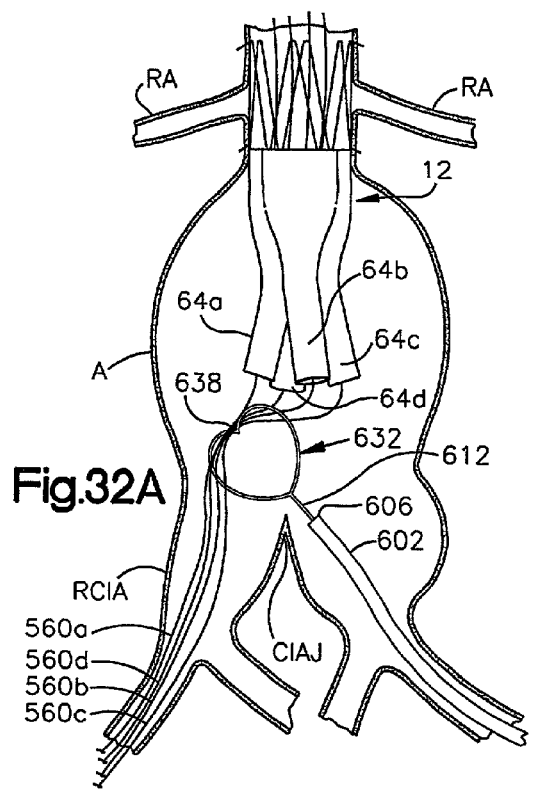
Fig.32A
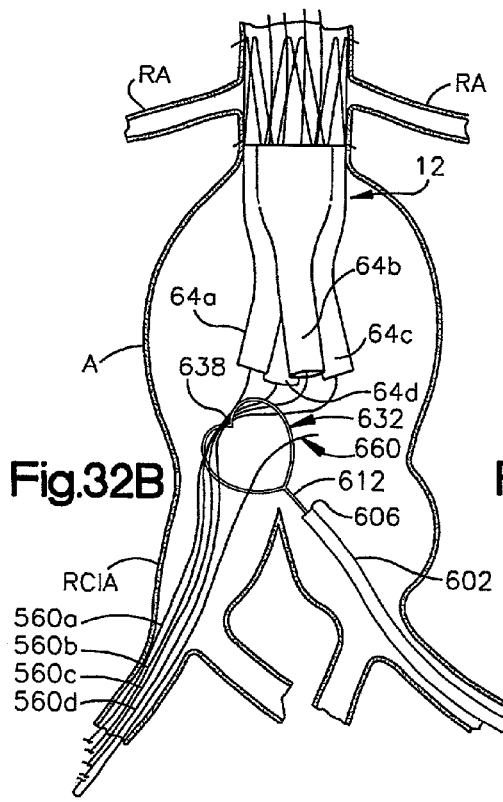
Fig.32B
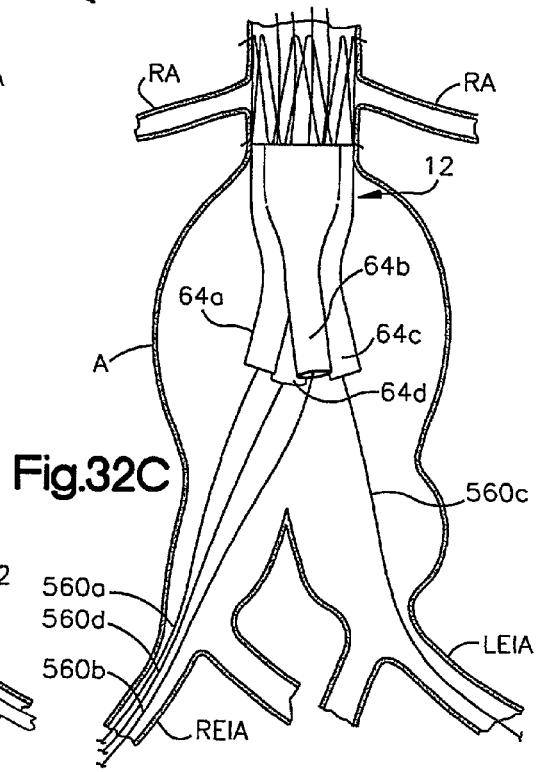
Fig.32C

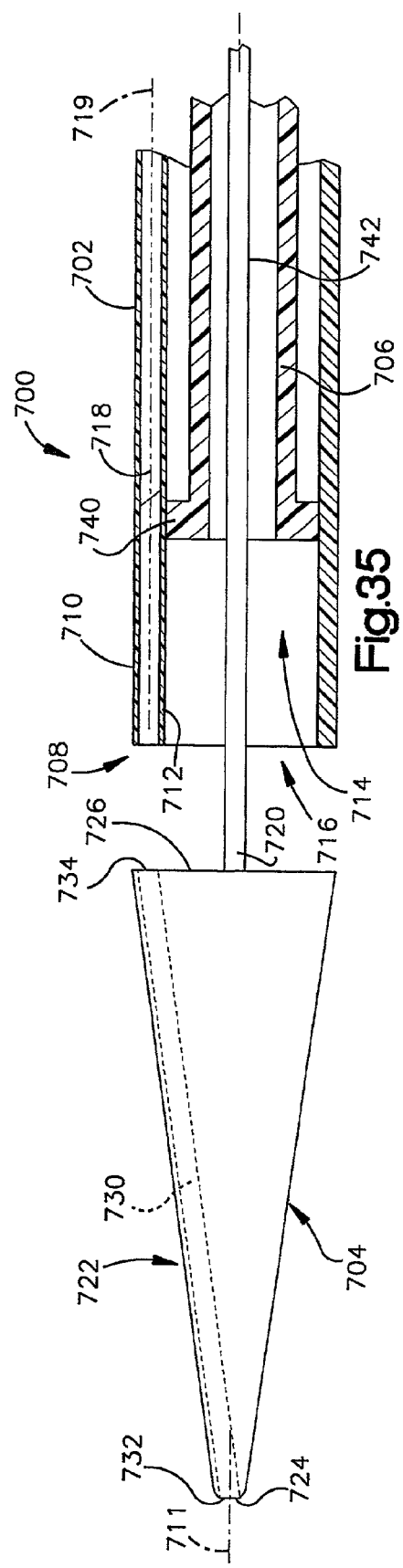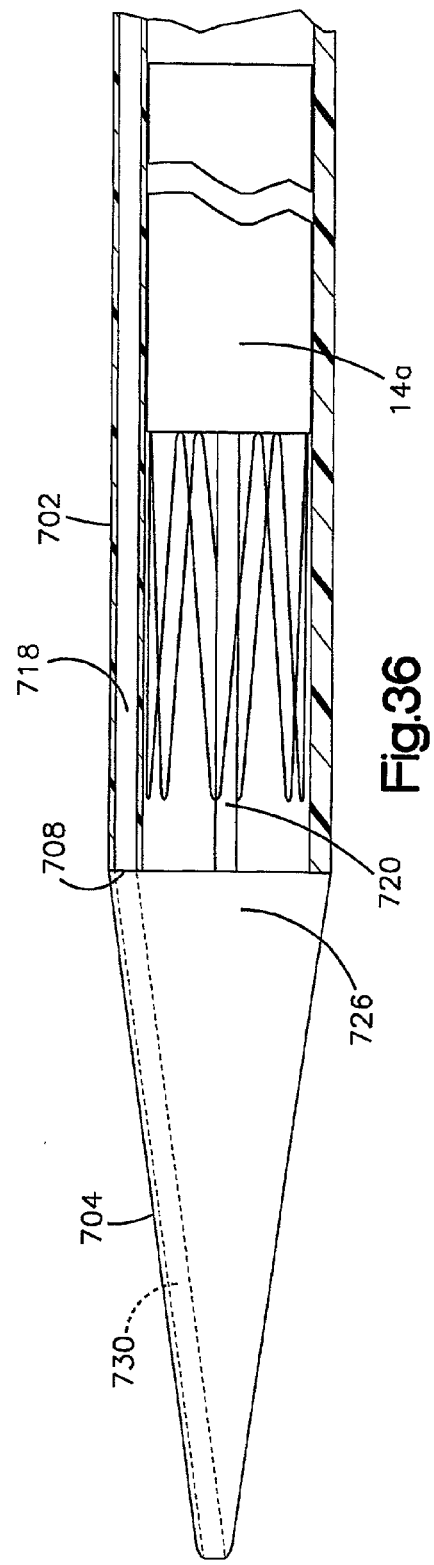

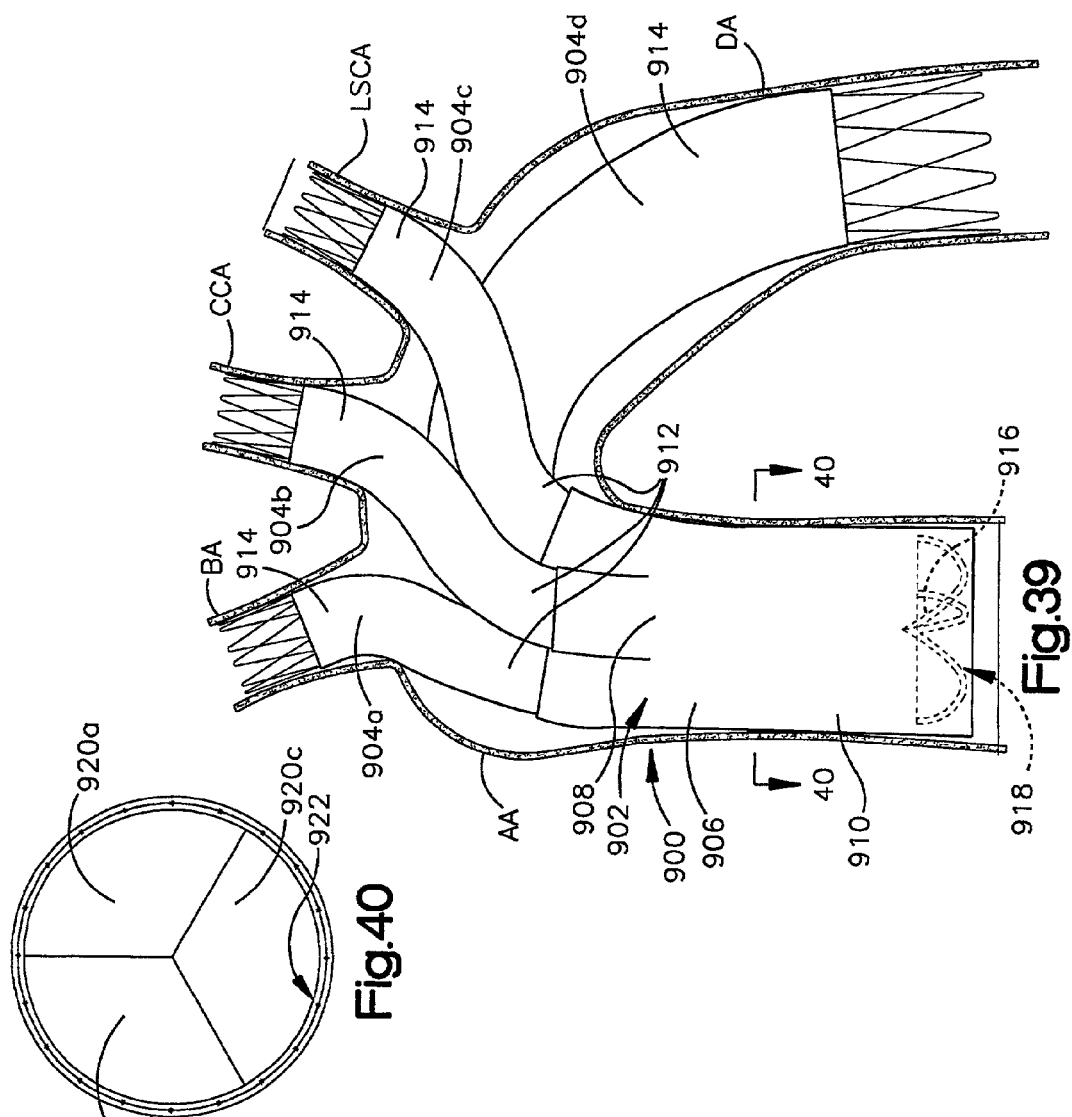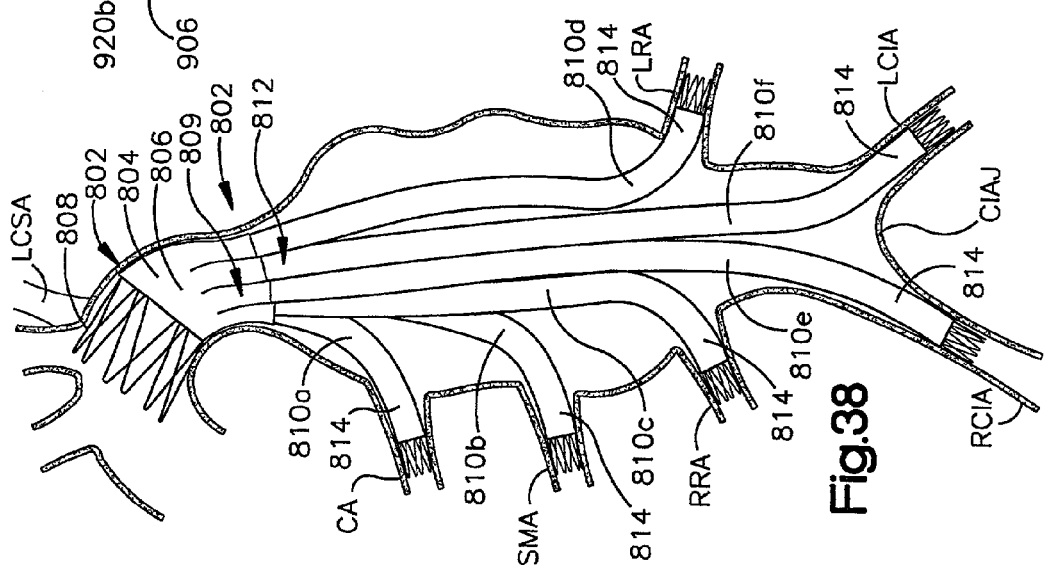

FURCATED ENDOVASCULAR PROSTHESIS

TECHNICAL FIELD

The present invention relates to an endovascular prosthesis, methods of manufacturing an endovascular prosthesis, and methods of and devices for deploying an endovascular prosthesis.

BACKGROUND OF THE INVENTION

Vascular aneurysms, which result from abnormal dilation of a blood vessel, can occur in any blood vessel. For instance, vascular aneurysms can occur in the aorta and peripheral arteries. The majority of aortic aneurysms occur in the abdominal aorta below the renal arteries. Often the abdominal aortic aneurysm extends into areas of bifurcation (e.g., the inferior end of the aorta where it bifurcates into the iliac arteries) or segments of the aorta from which other branch arteries extend.

Techniques have been developed for repairing abdominal aortic aneurysms by intraluminally delivering an endovascular graft to the aneurysm site through the use of a catheter-based delivery system. The endovascular grafts typically comprise a tube of pliable material (e.g., expanded polytetrafluoroethylene (ePTFE) or woven polyester) in combination with a graft anchoring component, which operates to hold the tubular graft in its intended position within the aorta. Most commonly, the graft anchoring component is formed of a stent or frame that is radially expandable to exert outwardly directing radial pressure against the surrounding blood vessel wall. The stent or frame can be either attached to or incorporated into the body of the tubular graft or provided separate from the graft and deployed within the graft.

Unfortunately, not all patients diagnosed with abdominal aortic aneurysms are considered to be candidates for endovascular grafting. Most endovascular grafts, which have been designed for treating abdominal aortic aneurysms, require the patient being treated have a proximal aortic neck inferior the renal arteries of at least 1 cm in length and a distal iliac neck less than 2.0 cm in diameter.

Additionally, the deployment of endovascular grafts within regions of the aorta from which the renal, superior mesenteric, celiac, intercostal, and/or subclavian arteries extend present additional technical challenges because, in those cases, it is advantageous to design, implant, and maintain, the endovascular graft in a manner which does not impair the flow of blood into these arteries.

SUMMARY OF THE INVENTION

The present invention is an endovascular prosthesis that includes a first end, a furcated second end, and an anchoring means. The first end has a longitudinally extending central lumen and means for laterally supporting the first end. The furcated second end includes at least two branches that extend from an intersection of the furcated second end. Each of the at least two branches includes a longitudinal support means and a branch lumen in fluid communication with the central lumen of the first end. The anchoring means secures the first end within a vasculature.

According to one aspect of the present invention, the first end includes a graft layer. The means for laterally supporting the first end is attached to the graft layer of the first end.

According to another aspect of the present invention, each of the at least two branches has a substantially equal length and includes a graft layer. The longitudinal support means of each of the branches is attached to each graft layer of the branches.

In a further aspect of the present invention, the endovascular prosthesis comprises at least two outflow limbs. The at least two outflow limbs each have a first end, a second end, and a lumen extending between the first end and second end. The first ends of each of the outflow limbs are capable of being connected to the at least two branches to allow fluid flow from the at least two branches through the outflow limbs.

According to another aspect of the present invention, the furcated second end includes at least three branches that extend from an intersection of the furcated second end. Each of the at least three branches includes a longitudinal support means and a branch lumen in fluid communication with the central lumen of the first end.

In a further aspect of the present invention, the endovascular prosthesis comprises at least three outflow limbs. The at least three outflow limbs each have a first end, a second end, and a lumen extending between the first end and second end. The first ends of each of the outflow limbs are capable of being connected to the at least three branches to allow fluid flow from the at least three branches through the outflow limbs.

Preferably, the endovascular prosthesis of the present invention is used to treat an abdominal aortic aneurysm that extends from a portion of the aorta caudal the renal arteries to the aorta iliac junction.

The present invention also provides a method for construction of an endovascular prosthesis with at least two outflow branches. According to the inventive method, at least two grafts are provided. Each of the at least two grafts has a first end, a second end, and a lumen extending longitudinally between the first end and the second end. The first end of each of the at least two grafts includes a means for laterally supporting the first end. The second end of each of the at least two grafts includes means for longitudinally supporting the second end. The first ends of each of the at least two grafts are deformed to produce a connection surface on each of the at least two grafts. The connection surfaces of each of the at least two grafts are joined to form an endovascular prosthesis with at least two outflow lumens that are in fluid communication with a central lumen.

In an alternative method of constructing an endovascular prosthesis with at least two outflow branches, a main graft is provided. The main graft has a first end, a second end, and a main lumen extending longitudinally between the first end the second end of the main graft. The main graft includes a means for laterally supporting the main graft. At least two branch grafts are provided. Each of the at least two branch grafts has a first end, a second end, and a lumen extending longitudinally between the first end and the second end of each of the branch grafts. Each of the at least two branch grafts includes a means for longitudinally supporting each of the branch grafts. The first ends of each of the at least two branch grafts are connected to the second end of the main graft to form an endovascular prosthesis with at least two branch lumens that are in fluid communication with a main lumen.

BRIEF DESCRIPTION OF THE DRAWINGS

The foregoing and other features of the present invention will become apparent to those skilled in the art to which the present invention relates upon reading the following description with references to the accompanying drawings, in which:

FIG. 1 is a perspective view of a multi-furcated endovascular prosthesis in accordance with the present invention;

FIG. 2 is a perspective view of the aortic component of FIG. 1;

FIG. 3 is a cross-sectional view taken along line 3—3 of FIG. 2;

FIG. 4 is a cut-away view of the trunk portion of FIG. 2;

FIG. 5 is a sectional view of the aortic component of FIG. 2;

FIG. 6 is a cut-away view of a branch of FIG. 2;

FIG. 7 is a cross-sectional view taken along line 7—7 in FIG. 6;

FIG. 8 is a perspective view of the anchoring means of FIG. 2;

FIGS. 9a–9b illustrate a first method of constructing the aortic component in accordance with the present invention;

FIGS. 10a–10d illustrate a second method of constructing an aortic component in accordance with the present invention;

FIG. 11 is a perspective view of an outflow limb of FIG. 1;

FIG. 12 is a cross-sectional view taken along line 12—12 in FIG. 11;

FIG. 13 is a partial sectional view of the end of the outflow limb of FIG. 11 inserted in a branch of the aortic component;

FIG. 14 is an enlarged perspective of an alternate embodiment of the end of the outflow limb;

FIG. 15 is a perspective view of a first embodiment of a delivery system for deploying the aortic component in accordance with the present invention;

FIG. 16 is an enlarged sectional view of the nosecone, cartridge sheath, and pusher rod of FIG. 15;

FIG. 17 is an enlarged perspective view of the nosecone and the cartridge sheath of FIG. 15;

FIG. 18 is a perspective view illustrating the aortic component with fine metallic guide wires and fine sutures;

FIG. 19 is a perspective view illustrating an alternate embodiment of the aortic component with the fine sutures;

FIG. 20 is a partial sectional view illustrating a radially compressed aortic component loaded in the delivery system of FIG. 15;

FIGS. 21a–21d illustrate a method of deploying the aortic component to treat an abdominal aortic aneurysm using the delivery system of FIG. 15;

FIG. 22 is a perspective view of a second embodiment of a delivery system for deploying the aortic component in accordance with the present invention;

FIG. 23 is an enlarged partial sectional view of the nosecone and cartridge sheath of FIG. 22;

FIG. 24 is and enlarged sectional view of the nosecone, cartridge sheath, and pusher rod of FIG. 22;

FIG. 25 is a partial sectional view illustrating a radially compressed aortic component loaded in the delivery system of FIG. 22;

FIGS. 26a–26b illustrate a method of deploying the aortic component to treat an abdominal aortic aneurysm using the second embodiment of the delivery system;

FIGS. 27a–27c illustrate a method of placing the guide wires that extend through the branches of the aortic component into separate branch arteries of the aorta;

FIG. 28 is a perspective view of a surgical snare instrument in accordance with the present invention;

FIG. 29 is an enlarged partial sectional view of the surgical snare instrument of FIG. 28;

FIG. 30 is an enlarged view of the wire loop of FIG. 28 in an open configuration;

FIG. 31 is an enlarged view of the wire loop of FIG. 28 withdrawn into the surgical snare instrument;

FIGS. 32a–32c illustrate a method of capturing a guide wire using the surgical snare instrument of FIG. 28;

FIG. 33 is an enlarged view of a guide wire with a hinge;

FIGS. 34a–34b illustrate a method of capturing the guide wire of FIG. 33 with the surgical snare instrument of FIG. 28;

FIG. 35 is a partial sectional view of a delivery system for deploying an outflow limb in accordance with the present invention;

FIG. 36 is a partial sectional view illustrating a radially collapsed outflow limb loaded in the delivery system of FIG. 35;

FIG. 38 illustrates an alternate embodiment of a multi-furcated endovascular prosthesis used to treat a thoracoabdominal aneurysm;

FIG. 39 illustrates another embodiment of a multi-furcated endovascular prosthesis used to treat an ascending aortic aneurysm; and FIG. 40 is a cross-sectional view taken along line 40—40 in FIG. 39.

DETAILED DESCRIPTION OF THE INVENTION

Figure 21D:
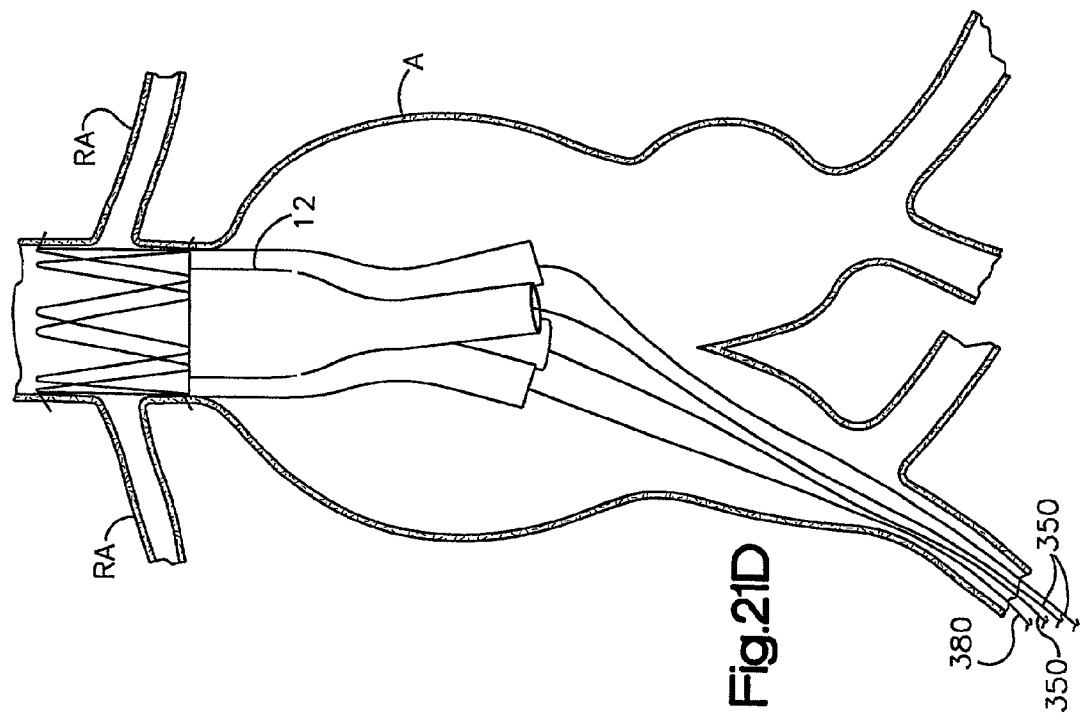

The present invention relates to apparatuses and methods for treating vascular diseases. In particular, the present invention relates to a furcated endovascular prosthesis for treating an aortic aneurysm that extends close to or into branching arteries of the aorta. By "furcated" it is meant the endovascular prosthesis includes a trunk lumen and at least two branch lumens that extend from the trunk lumen.

FIG. 1 is a perspective view of a furcated endovascular prosthesis 10 in accordance with one embodiment of the present invention. The furcated endovascular prosthesis 10 includes an aortic component 12 and four outflow limbs 14(a–d) that extend from the aortic component 12.

Referring to FIGS. 1 and 2, the aortic component 12 includes a trunk portion 16, a furcated portion 18, and an anchoring means 20. The trunk portion 16 is tubular and comprises a first end 22 and a second end 24. The first end 22 defines an orifice 26. Referring to FIG. 3, the trunk portion 16 has an inner surface 28 and an outer surface 30. The inner surface 28 is annular and defines a lumen 32 that extends along a longitudinal axis 34 between the first end 22 and the second end 24 of the trunk portion 16. The outer surface 30 is annular and extends co-axially with the inner surface 28.

The outer diameter of the trunk portion 16 is about 2.0 to about 3.5 cm. The length of the trunk portion 16 is about 2.0 to about 3.0 cm. The foregoing dimensions of the trunk portion 16 are for an endovascular prosthesis that is used to repair a typical abdominal aortic aneurysm. The dimensions may vary if the abdominal aortic aneurysm is atypical and/or if the endovascular prothesis is placed at other locations within the aorta or is placed within other blood vessels.

Referring to FIG. 3 and FIG. 4, the trunk portion 16 includes an inner graft layer 36, an outer graft layer 38, and an expandable support member 40, which is attached to the inner graft layer and the outer graft layer. The inner graft layer 36 has an inner surface 42 and an outer surface 44 that extend co-axially between the first end 22 and the second end 24 of the trunk portion 16. The inner surface 42 of the inner graft layer 36 defines the inner surface 28 of the trunk portion 16 and provides a smooth fluid flow surface to facilitate non-turbulent fluid flow through the lumen 32 of trunk portion 16. Non-turbulent fluid flow is of particular importance to proper blood flow. Surfaces that increase blood flow turbulence have associated increased incidence of thrombus formation.

The outer graft layer 38 of the trunk portion 16 has an inner surface 46 and an outer surface 48 that extend co-axially from the first end 32 to the second end 24 of the trunk portion 16. The outer surface 48 of the outer graft layer 38 defines the outer surface 30 of the trunk portion 16. The outer graft layer 38 is co-axially aligned over the inner graft layer 36 so that the outer graft layer 38 substantially covers the outer surface 44 of the inner graft layer 36.

The inner graft layer 36 and the outer graft layer 38 of the trunk portion 16 are preferably formed from a biocompatible fabric having sufficient strength to withstand the surgical implantation of the endovascular prosthesis 10 and to withstand the blood pressure and other biomechanical forces that are exerted on the endovascular prosthesis. The biocompatible fabric can be formed by weaving or extruding a biocompatible material. Examples of biocompatible materials, which can be weaved or extruded to form the biocompatible fabric, are polyethylene, polypropylene, polyurethane, polyglycolic acid, polyesters, polyamides, polyflurocarbons, copolymers thereof, and mixtures thereof. Preferred biocompatible materials, which can be used to form the biocompatible fabric, are polyesters, such as DACRON and MYLAR, and polyflurocarbons, such as polytetrafluoethylene and expanded polytetrafluorethylene (ePTFE).

More preferably, the biocompatible fabric is an expanded polytetraflourethylene fabric (ePTFE) that is formed, in a manner not shown, by extruding a polytetrafluoroethylene-lubricant mixture through a ram extruder into a tubular-shaped extrudate and longitudinally expanding the tubular extrudate to yield a uniaxially oriented fibril microstructure in which substantially all of the fibrils in the expanded polyetetrafluoroethylene (ePTFE) microstructure are oriented parallel to one another in the axis of longitudinal expansion.

To reduce the bulk and facilitate the intraluminal delivery of the aortic component 12 of the endovascular prosthesis 10 the inner graft layer 36 and the outer graft layer 38 each, preferably, have a thickness of about 0.1 mm. It will be appreciated that the present invention can be practiced with an inner graft layer and an outer graft layer which have thicknesses greater than about 0.1 mm or less than about 0.1 mm.

Referring to FIGS. 3 and 4, the expandable support member 40 is sandwiched between the inner graft layer 36 and the outer graft layer 38 and laterally supports the inner graft layer 36 and the outer graft layer 38. An inner surface 50 of the expandable support member 40 engages the outer surface 44 of the inner graft layer 36 substantially along its entire length. An outer surface 52 of the expandable support member 40 engages the inner surface 46 of the outer graft layer 38 substantially along its entire length.

The expandable support member 40 comprises at least one radially expandable stent, and preferably, a plurality of axially aligned radially expandable stents. The stent(s) can have a construction similar to any radially expandable stent well-known in the art, which is suitable for vascular implantation.

FIG. 4 illustrates an example of a expandable support member that includes a plurality or axially aligned radially expandable stents 54. Each stent 54 includes an annular support beam 56. Each annular support beam 56 has a generally sinusoidal shape. The wavelength of each of the support beams 56 is identical or essentially identical to the wavelength of the adjacent axially aligned support beams 56.

Each stent 54 is preferably formed of a metal that has super-elastic properties. Preferred metals include nickel-titanium alloys. An example of a nickel-titanium alloy is NITINOL. Nickel-titanium alloys are preferred as metals for the stent 54 because of their ability to withstand a significant amount of bending and flexing and yet return to their original shape without deformation. Nickel-titanium alloys are also characterized by their ability to be transformed from one shape with an austenitic crystal structure to another shape with a stress induced martensitic crystal structure at certain temperatures, and to return elastically to the one shape with the austenitic crystal structure when the stress is released. These alternating crystal structures provide nickel-titanium alloys with their super-elastic properties. Examples of other metals that have super-elastic properties are cobalt-chrome alloys (e.g., ELGILOY) and platinum-tungsten alloys.

Other materials that can be used to form each stent 54 are metals, such as stainless steel, and polymeric materials, such as nylon and engineering plastics, such as thermotropic liquid crystal polymers. Thermotropic liquid crystal polymers are high molecular weight materials that can exist in a so-called "liquid crystalline state" where the material has some of the properties of a liquid (in that it can flow) but retains the long range molecular order of a crystal. Thermotropic liquid crystal polymers may be prepared from monomers such as p,p'-dihydroxy-polynuclear-aromatics or dicarboxy-polynuclear aromatics.

Although the trunk portion 18 is illustrated as including both an inner graft layer and an outer graft layer, the trunk portion may include only a single graft layer (not shown). If a single graft layer is used, the expandable support member can be attached to the inner surface or the outer surface of the single graft layer. The expandable support member can be attached to the single graft layer by attachment means, such as sutures glues, and chemical bonding. Preferably, the expandable support member is attached to the outer surface of the single graft layer so that the trunk portion has an inner surface that provides a smooth fluid flow surface through the trunk portion.

Referring to FIG. 2, the furcated portion 18 extends from the second end 24 of the trunk portion 16 along the longitudinal axis 34. The furcated portion 18 includes four branches 64(a–d). Referring to FIG. 5, which is a partial sectional view of FIG. 2, the four branches 64(a–d) of the furcated portion 18 extend from an intersection 66 lying in a plane perpendicular to the longitudinal axis 34.

Referring to FIG. 1, each branch 64(a–d) has a substantially equal length and serves as a point of fixation and sealing for a separate outflow limb 14(a–d). The length of each branch 64(a–d) can be greater than, less than, or equal to the length of the trunk portion 16 of the aortic component 12. The diameter of each branch can be the same or different. Preferably, the length of each branch 64(a–d) is about 2.5 cm, and the outer diameter of each branch 64(a–d) is about 1 cm.

As with the trunk portion 16 of the aortic component 12, the foregoing dimensions of the branches 64(a–d) of the furcated portion 18 are for an endovascular prosthesis that is used to repair a typical abdominal aortic aneurysm. The dimensions may vary if the abdominal aortic aneurysm is atypical and/or if the endovascular prosthesis is placed at other locations within the aorta. Moreover, although the furcated portion 18 is illustrated as having four branches 64 that extend from the intersection 66, the furcated portion 18 could have two branches, three branches, five branches, or more than five branches that extend from the intersection 66.

The four branches 64(a–d) of the furcated portion 18 illustrated in FIG. 2 all have a similar construction. Accordingly, the construction of only one branch 64 will be discussed below.

FIG. 6 illustrates one branch 64 of the furcated portion 18. The branch 64 is tubular and has an inner surface 70 and outer surface 72 that extend along an axis 74 from the intersection 66 (FIG. 5) to an open end 76. The open end 76 is sized to receive an outflow limb 14 for fixation. The inner surface 70 of the branch 64 is cylindrical and defines a branch lumen 78 (FIG. 7). The branch lumen 78 is in fluid communication with the trunk lumen 32 and extends from the intersection 66 to the open end 76.

Referring to FIG. 7, the branch 64 comprises an inner graft layer 80, an outer graft layer 82, and a means 84 for longitudinally supporting the inner graft layer 80 and the outer graft layer 82, which is attached to the inner graft layer and the outer graft layer. The inner graft layer 80 has an inner surface 86 and an outer surface 88 that extend co-axially from the intersection 66 of the furcated portion 18 to the open end 76 of the branch. The inner surface 86 of the inner graft layer 80 defines the inner surface 70 of the branch 64. The inner surface 70 of the inner graft layer 80 of the branch 64, like the inner surface 28 of the inner graft layer 36 of the trunk portion 16, provides a smooth fluid flow surface to facilitate non-turbulent fluid flow through the branch lumen 78.

The outer graft layer 82 has an inner surface 90 and an outer surface 92 that co-axially extend from the intersection 66 to the open end 76 of the branch 64. The outer graft layer 82 is co-axially aligned over the inner graft layer 80 so that the outer graft layer 82 substantially covers the outer surface 88 of the inner graft layer 80.

The inner graft layer 80 and the outer graft layer 82 of the branch 64 are formed from a biocompatible fabric. The biocompatible fabric can be the same fabric used to form the inner graft layer 36 and outer graft layer 38 of the trunk portion 16 or a different biocompatible fabric. Preferably, the biocompatible fabric used to form the inner graft layer 80 and outer graft layer 82 of the branch 64 is the same as the biocompatible fabric used to form the inner graft layer 36 and the outer graft layer 38 of the trunk portion 16 of the aortic component 12.

The means 84 for longitudinally supporting the inner graft layer 80 and the outer graft layer 82 comprises a longitudinal support structure that can be sandwiched between the inner graft layer 80 and the outer graft layer 82. The longitudinal support structure, as illustrated in FIG. 6, is a rod 84 that axially extends substantially the length of the branch 64. The rod 84 can be formed of a metal, such as Nitinol or stainless steel, or of a polymeric material.

Although the rod 84 is illustrated as being sandwiched between the inner graft layer 80 and the outer graft layer 82, the rod 84 may be attached to the inner surface 70 or the outer surface 72 of the branch 64 to provide longitudinal support to the branch. The rod 84 can be attached to the inner surface 70 or the outer surface 72 of the branch 64 by attachment means, such as sutures, glues, and chemical bonding means.

Moreover, although the branch 64 is illustrated as including both an inner graft layer and an outer graft layer, the branch may include only a single graft layer (not shown). If a single graft layer is used, the longitudinal support can be attached to the inner surface or the outer surface of the single graft layer. The longitudinal support can be attached to the innner or the outer surface of the single graft layer of the branch by attachment means, such as sutures, glues, and chemical bonding means.

Referring to FIG. 2, the anchoring means 20 of the aortic component 12 extends from the first end 22 of the trunk portion 16. The anchoring means 20 secures the aortic component 12 of the endovascular prosthesis 10 to the wall of the aorta in which the aortic component is deployed.

The anchoring means 20 comprises a radially expandable bare stent 88. By "bare stent" it is meant that the stent is not covered with a graft layer or fabric that would inhibit radial flow of fluid through the stent. The bare stent 88 is substantially tubular and can have a construction similar to any vascular stent known in the art.

FIG. 8 illustrates one example of a bare stent 88. The bare stent 88 includes an annular support beam 90 that has a generally sinusoidal shape. The bare stent 88 is preferably formed of a metal that has super-elastic properties, but may also be formed of a polymeric material.

The bare stent 88, preferably, includes wall-engaging members 100. The wall-engaging members 100 comprise pairs of axially aligned barbs 100 (or hooks) that extend outwardly from the bare stent 88 and in a direction toward the first end 22 of the trunk portion 16 of the aortic component 12. When the bare stent 88 is radially expanded, the barbs 100 engage the wall of the aorta and prevent migration of the aortic component 12 within the aorta.

The pairs of axially aligned barbs 100 are secured to the bare stent 88 by suitable means, such as welding. Alternatively, the pairs of axially aligned barbs 100 can be an integral part of the bare stent. Preferably, at least two pair of axially aligned barbs 100 are secured to essentially diametrically opposed areas of the bare stent 88. The length of each barb 100 is that length which is sufficient to penetrate into the wall of the aorta where the endovascular prosthesis 10 is to be placed.

Referring to FIG. 1, the aortic component 12 can also include a first series of radiomarkers 102 that are positioned about the periphery of the trunk portion 16 of the aortic component 12 and a second series of radiomarkers 104 that are positioned about the periphery of each of the branches 64(a–d), of the aortic component 12. As is well-known in the art, the radiomarkers 102 and 104, when viewed under fluoroscopy, enable the surgeon to identify and properly locate the aortic component 12 during surgical placement of the aortic component 12. The radiomarkers 102 and 104 may be formed from biocompatible metal such as stainless steel, gold, or platinum-iridium, which are radioopaque, or from radioopaque polymers.

FIGS. 9A–9B illustrate one method of forming the aortic component 12 of the present invention. According to the method of FIGS. 9A–9B, four stent-grafts 110 are provided and have a similar construction. FIG. 9A illustrates one of the stent-grafts 110. The stent-graft 110 consists of a tubular member 112 that has an interior surface 114 and an exterior surface 116 extending between first and second ends 118 and 120. The tubular member 112 includes a first tubular graft layer 122 and a second tubular graft layer 124 that is co-axially aligned over the first tubular graft layer.

The tubular member 112 further includes a radially expandable support member 126 and a longitudinal support member 128. The radially expandable support member 126 comprises a plurality of axially aligned stents while the longitudinal support member 128 comprises an elongated rod. The radially expandable support member 126 is sandwiched between the first tubular graft layer 122 and the second tubular graft layer 124 at the first end 118 of the tubular member 112 while the longitudinal support member 128 is sandwiched between the first tubular graft layer 122 and the second tubular graft layer 124 at the second end 126 of the tubular member 112.

The stent-graft 110 can be made by well known stent-graft forming techniques. For example, in one method (not shown) a first tubular graft layer is loaded over a mandrel. The first tubular graft layer is preferably an extruded polytetrafluoroethylene lubricant mixture. A section of the first tubular graft layer is then wrapped with wire or tape to prevent migration of the first tubular graft layer on the mandrel. A plurality of stents are dilated, loaded over, and then crimped on a first end of the first tubular graft layer. An elongated rod is attached to the second end of the first tubular graft layer so that the elongated rod extends, axially, along the second portion of the tubular graft layer. The elongated rod can be attached to the graft layer by suturing or by gluing the elongated rod to the first tubular graft layer.

A second tubular graft layer is then loaded over the crimped stents, the longitudinal rod, and the first tubular graft layer so that the second tubular graft layer is co-axially aligned with the first tubular graft layer. After loading the second tubular graft layer over the crimped stents, the longitudinal rod, and the first tubular graft layer, circumferential or radial pressure is applied to the stent graft assembly either by wrapping the assembly with a helical wrap of an expanded polytetrafluoroethylene (ePTFE) tape or TEFLON tape, or placing the stent-graft assembly in a cylindrical press and exerting a radial pressure to the abluminal surface of the stent-graft assembly. The applied pressure causes the first and second tubular graft layers to contact and mechanically bond to one another. The stent-graft assembly is then heated to the sintering temperature of the tubular grafts layer to sinter the first and second tubular layers into a substantially monolithic covering, which encapsulates the stent and the longitudinal support member. After heating at the sintering temperature of the expanded polytetrafluorethylene, the stent-graft assembly is allowed to cool and the tape and wire wraps are removed from the assembly.

Each of the four stent-grafts 110 is then cut, to remove a section (not shown) of each stent-graft and to create a "V" shaped opening 128 that extends from the first end 118 of each stent-graft. The stent-grafts 110 are preferably cut by a laser cutting means but could also be cut by other cutting means, such as a shear.

FIG. 9B shows that the stent-graft 110 has been cut by a laser cutting means to form the "V" shaped opening 128. The "V" shaped opening 128 axially extends from the first end 118 of the stent-graft 110 to a point on the stent-graft just beyond the stent 126 but before the longitudinal support member 128. The "V" shaped opening 128 of the stent-graft 110 has a first edge 130 and a second edge 132 that extend to an apex 134. The first edge 130 defines a first connection surface 131 and the second edge 132 defines a second connection surface 133.

As shown in FIG. 5, the four stent-grafts 110 with the "V" shaped openings 128 are arranged about the central axis 34 so that apexes 134 of the "V" shaped openings are aligned and the first connection surface 131 of each stent graft is aligned with the second connection surface 133 of another stent graft. The first connection surface 131 of one of the stent-grafts 110 is joined to the second connection surface 133 of another stent-graft to form an aortic component that has an annular trunk portion 16 which transitions into the four separate branches 64. The first connection surface 131 and the second connection surface 131 may be joined by a variety processes well known in the art, such as suturing, sintering, gluing, and spot welding.

A bare stent, such as the bare stent 88, is then attached to the trunk portion 16 of the endovascular prosthesis 10 by a suitable method, such as suturing or gluing, to form the aortic component 12 of FIG. 2.

FIGS. 10A–10D illustrate a second method of forming the aortic component 12 of the present invention. According to the second method, a main stent-graft 140 and four branch grafts 160(a–d) are provided. FIG. 10A shows that the main stent-graft 140 comprises a tubular member 142 that has an inner surface 144 and an outer surface 146 that extend along a longitudinal axis 148 between first and second ends 150 and 152. The inner surface 144 of the main stent-graft 140 defines a main lumen 154 that extends between the first end 150 and the second end 152.

The tubular member 142 also includes a first tubular graft layer 156 and a second tubular graft layer 157 that is co-axially aligned over the first tubular graft layer 156. The first tubular graft layer 156 and the second tubular graft layer 157 extend from the first end 150 to the second end 152 of the tubular member 142.

The tubular member 142 further includes a radially expandable support member 158 that is sandwiched between the first tubular graft layer 156 and the second tubular graft layer 157 and extends from the first end 150 to the second end 152 of the tubular member 142.

The main stent-graft 110 can be made by well-known stent graft forming techniques. For example, in one method (not shown), a first tubular graft layer is loaded over a mandrel. A plurality of stents are dilated, loaded over, and crimped on the first tubular graft layer. A second tubular graft layer is loaded over the crimped stents, and the first tubular graft layer so that the second tubular graft layer is coaxially aligned with the first tubular graft layer. The stent-graft assembly is then heated to the sintering temperature of the tubular grafts layer to bond and sinter the first and second tubular graft layers into a substantially monolithic covering, which encapsulates the stents.

The four branch grafts 160(a–d) each have a similar construction. FIG. 10B illustrates one of the branch grafts 160 in accordance with the present invention. The branch graft 160 is tubular and has an inner surface 162 and an outer surface 164 axially extending along a longitudinal axis 166 between the first and second ends 168 and 170. The inner surface 162 of the branch graft 160 defines a branch lumen 161 that extends between the first and second ends 168 and 170 of the branch graft 160.

The branch graft 160 includes a first tubular graft layer 172 and a second tubular graft layer 174 that is co-axially aligned over the first tubular graft layer 172. The first tubular graft layer 172 and the second tubular graft layer 174 extend from the first end 168 to the second end 170 of the branch graft 160. The branch graft 160 further includes an axially extending elongated rod 176 that is sandwiched between the first tubular graft layer 172 and the second tubular graft layer 174 and extends parallel to the axis 166.

The branch graft 160 can be made by well-known graft forming techniques. For example in one method (not shown), the first tubular graft layer is loaded over a mandrel. An elongated rod is axially aligned on the first tubular graft layer and bonded to the first tubular graft layer. A second tubular graft layer is loaded over the longitudinal rod, and the first tubular graft layer so that the second tubular graft layer is co-axially aligned with the first tubular graft layer. The branch graft assembly is then heated to the sintering temperature of the tubular grafts layer to bond and sinter the first and second tubular graft layers into a substantially monolithic covering, which encapsulates the elongated rod.

Referring to FIG. 10C, each of the four branch grafts 160(a–d) is then attached to the second end 152 of the main stent-graft 140 so that each branch graft axially extends from the main stent-graft 140. The four branch 160(a–d) can be attached to the second end 152 of the main stent-graft 140 by crimping the first ends of each branch graft 160(a–d) and joining a portion of outer surface of each of the crimped first ends of the branches. The first ends of the branch grafts can be joined by a suitable means, such as gluing, suturing, or sintering. The joined first ends of the branch graft are inserted in the main lumen at the second end of the main stent-graft. The second end of the main-stent graft is crimped around and bonded to the joined first ends of the branch grafts so as to secure and seal the main graft to the branch grafts. The joined branch grafts 160a, 160b, 160c and 160d can be bonded to the main stent-grafts 110 by a suitable process, such as gluing, suturing, or sintering.

As shown FIG. 10D, the four branch grafts 160(a–d) are attached to the main stent-graft 140 to form a furcated portion 170 which transitions the main lumen into four separate branch lumens 171(a–d). A bare stent is then attached to the first end 180 of the main stent-graft 140 by a suitable process, such as suturing or gluing, to form the aortic component.

Referring again to FIG. 1, the outflow limbs 14(a–d) are connected to the branches 64(a–d), respectively, of the aortic component 12. The outflow limbs 14(a–d) interconnect the branches 64(a–d) with the branch arteries of the aorta (i.e., the right (ipsilateral) external iliac artery, right (ipsilateral) internal iliac artery, left (contralateral) external iliac artery, and left (contralateral) internal iliac artery) to allow blood to flow from the aortic component 12 to the branch arteries. Although the outflow limbs 14(a–d) are illustrated as having similar lengths and diameters, the lengths and diameters of the outflow limbs will vary depending upon the distance from the specific branch to the specific branch artery, which the outflow limb interconnects, and the diameter of the specific branch artery.

FIG. 11 illustrates an exemplary embodiment of an outflow limb 14 in accordance with the present invention. The outflow limb 14 is tubular and comprises a main body 181 with an inner surface 180 and an outer surface 182 that extend along an axis 187 between a first end 184 and a second end 186 of the main body 181. The inner surface 180 of the outflow limb 14 defines a lumen 188 that extends through the outflow limb 14 the length of the outflow limb. The first end 184 of the outflow limb 14 defines an opening 189 in the first end 184 of the outflow limb 14. The main body 181 has an essentially uniform outer diameter between the first end 184 and the second end 186.

Referring to FIG. 12, the outflow limb 14, like the trunk portion 16 of the aortic component 12, includes an inner graft layer 190, an outer graft layer 192, and an expandable support member 194, which is attached to the inner graft layer 190 and the outer graft layer 192. An inner surface 196 of the inner graft layer 190 defines the inner surface 190 of the outflow limb 14 and an outer surface 198 of the outer graft layer 192 defines the outer surface 182 of the outflow limb 14. The outer graft layer 192 is coaxially aligned over the inner graft layer 190 so that the outer graft layer 192 substantially covers the inner graft layer 190.

The inner graft layer 190 and the outer graft layer 192 are formed from a biocompatible fabric. The biocompatible fabric can be the same fabric used to form the inner graft layer 36 and outer graft layer 38 of the trunk portion 16 of the aortic component 12 or a different biocompatible fabric. Preferably, the biocompatible fabric used to form the inner graft layer 190 and the outer graft layer 192 of the outflow limb 14 is the same biocompatible fabric used to from the inner graft layer 36 and the outer graft layer 38 of the trunk portion of the aortic component 16.

The expandable support member 194 of the outflow limb 14 is sandwiched between the inner graft layer 190 and the outer graft layer 192 and laterally supports the inner graft layer 190 and the outer graft layer 192 substantially the entire length of the inner graft layer 190 and the outer graft layer 192. The expandable support member 194 comprises a plurality of axially aligned radially expandable stents. The stents 194 can have a construction similar to any radially expandable stent well-known in the art. Preferably, the stents 194 have a construction similar to the stents 54 used to provide lateral support to the trunk portion 16 of aortic component 12.

Although the outflow limb is illustrated as including both an inner graft layer and an outer graft layer, the outflow limb may include only a single graft layer (not shown). If a single graft layer is used for the outflow limb, the expandable support member can be attached to the inner surface or the outer surface of the single graft layer. The expandable support member can be attached to the single graft layer by attachment means, such as sutures, glues, or chemical bonding. Preferably, the expandable support member is attached to the outer surface of the single graft layer so that the outflow limb has an inner surface that provides a smooth fluid flow surface through the outflow limb.

Referring again to FIG. 1, the first end 184 of each of the outflow limbs 14(a–d) articulates with a separate branch 64(a–d) of the furcated portion 18 of the aortic component 12. The first end 184 of the outflow limb 14 has an outer diameter that is essentially equal to or greater than the inner diameter of the branch lumen 171 of the branch 64 so that when the first end 184 of each outflow limb 14 is inserted within the branch lumen 171 of the branches 64 of the furcated portion 18 and expanded, the outer surface of the first end 184 of the outflow limb 14 engages the inner surface 70 of the branch 64.

Referring to FIG. 11, the first end 184 of outflow limb 14 can include wall-engaging members 200 that facilitate fixation of the outflow limb 14 to a branch 64 of the furcated portion 18 of the aortic component 12. The wall-engaging members 200 comprise pairs of axially aligned barbs 202 (or hooks). Preferably, one barb 202 of the pair extends in a direction toward the first end 184 of the outflow limb 14 while the other barb extends in a direction toward the second end 186 of the outflow limb 14. The pairs of axially aligned barbs 202 prevent distal and proximal migration of the outflow limb 14 when the outflow limb 14 is deployed within the branch 64 of the furcated portion 18 of the aortic component 12.

The pairs of axially aligned barbs 202 are preferably secured to the expandable support member 194 and extend through the outer tubular layer 192 of the outflow limb 14.

More preferably, two pair of axially aligned barbs 202 are positioned about the circumference of the first end 184 at diametrically opposed areas of the first end 184. The length of the barbs 202 is that length which is sufficient to penetrate the biocompatible fabric of the first and second graft layers 80 and 82 of the branch 64 in which the outflow limb 14 is to be placed.

FIG. 13 is an enlarged sectional view showing the first end 184 of the outflow limb 14 deployed within a branch lumen of a branch 64 of the furcated portion 18 of the aortic component 12. The branch 64 of the aortic component 12 overlaps the first end 184 of the outflow limb 64. The first end 184 of the outflow limb 14 includes two pairs of axially aligned barbs 202. The pairs of axially aligned barbs 202 extend from the first end 184 of the outflow limb 184 through the branch 64 of the furcated portion 18 of the aortic component 12. The pairs of axially aligned barbs 202 are preferably offset from the opening 189 of the first end 184 of the outflow limb 14. By offsetting the barbs 202 from the opening 189 of the first end 184 of the outflow limb 14, should the barbs tear the biocompatible fabric of the branch 64 of the aortic component, the overlapped biocompatible fabric of the first end of the outflow limb will seal the tear and prevent loss of fluids (i.e., blood) that flow through the branch 64 and the outflow limb 14.

Optionally, as shown in FIG. 14, which is an enlarged view of the first end 184 of the outflow limb 14 in accordance with another embodiment of the present invention, the first end 184 of the outflow limb 14 can be tapered radially outward so that the outer diameter of the first end increases from the outer diameter of the main body 181 of the outflow limb 14 to the opening 189. The angle of taper is from about 2° to about 15° from the axis 187. The increase in outer diameter of the first end 184 of the outflow limb 14 prevents distal migration of the outflow limb from the branch 64 of the furcated portion once the outflow limb has been deployed within a branch 64 of the furcated portion 18.

Additionally, a biocompatible glue (not shown) can be provided on the outer surface of the first end 184 of the outflow limb or on the inner surface of a branch 64 of the furcated portion 18 prior to connection of the outflow limb 14 to the branch 64. Once the first end 184 of the outflow limb is positioned within the branch 64 of the furcated portion 18, the biocompatible glue secures (i.e., prevents distal and proximal migration) the outflow limb to the branch.

Referring to FIG. 11, the second end 186 of the outflow limb 14 can also be tapered radially outward so that the outer diameter of the second end 186 increases from the outer diameter of the main body 181 of the outflow limb. The angle of taper is from about 2° to about 15° from the axis 187. The increase in outer diameter of the second end 186 of the outflow limb is advantageous, because in situations where the aneurysm extends from the aorta into a branch artery of the aorta, the increased outer diameter of the second end 186 allows the second end 186 to be more readily secured within the branch artery.

The second end 186 of the outflow limb preferably includes an anchoring means 210. The anchoring means 210 secures the second end 186 of the outflow limb 14 to a wall of a branch artery in which the second end 186 of the outflow limb 14 is to be disposed. The anchoring means 210 comprises a bare stent 212. The bare stent 212 is tubular and extends axially from the second end 186 of the outflow limb. The bare stent 212 has a construction similar to the bare stent 20 of the aortic component 12.

The bare stent 212 of the outflow limb 14 preferably includes wall-engaging members 214. The wall-engaging members 214 comprise pairs of axially aligned barbs 216 (or hooks) that extend outwardly from the bare stent 212 and in direction toward the second end 186 of the outflow limb 14. When the bare stent 212 is radially expanded, the barbs 216 engage the wall of the branch artery in which the outflow limb is deployed and prevent migration of the second end 186 of the outflow limb 14 from the branch artery.

The pairs of axially aligned barbs 216 are secured to the bare stent 212 by suitable means, such as welding or glue. Alternatively, the pairs of axially aligned barbed can be an integral part of the bare stent. The length of the barbs 216 is sufficient to penetrate into the wall of the branch artery in which the second end of the outflow limb 14 is to be placed.

The outflow limb 14 can also include a series of radiomarkers (not shown) positioned about the peripheries of the first end 182 and the second end 186 of the outflow limb. The radiomarkers, as well known in the art, when viewed under fluoroscopy, enable the surgeon to identify and properly locate the outflow limb 14 during surgery. The radiomarkers may be formed from biocompatible metal such as stainless steel, gold, or platinum-iridium, which are radioopaque or from radioopaque polymers.

The outflow limb 14 can be made by well-known stent-graft forming techniques. For example, in one method (not shown) the outflow limb 14 is made by loading a first tubular graft layer of biocompatible fabric over a mandrel. The first tubular layer is preferably made by extruding a polytetrafluoroethylene (PTFE) lubricant mixture through a ram extruder into a tubular extrudate. A section of the first tubular graft layer is then wrapped with wire or tape to prevent migration of the first tubular graft layer on the mandrel. A plurality of radially expandable stents with first and second ends are then dilated, loaded over, and crimped on the first tubular layer. The stents should substantially cover the first tubular graft layer.

A second tubular graft layer is then loaded over the crimped stents and the first tubular graft layer so that the second tubular graft layer is co-axially aligned with the first tubular graft layer. After loading the second tubular graft layer over the crimped stent and the first tubular graft layer, circumferential or radial pressure is applied to the stent-graft assembly and the stent-graft assembly is heated to sinter the first and second tubular graft layers into a substantially monolithic covering, which encapsulates the stents and forms the outflow limb 14.

Methods of introducing and deploying the furcated endovascular prosthesis 10 to treat an abdominal aortic aneurysm that extends from a portion of the aorta caudal the renal arteries to the aorta iliac junction will now be described. The described methods assume that the expandable support members and anchoring means of the endovascular prosthesis 10 are tubular stents, formed from a shape-memory metal, and that the expandable support members and the anchoring means will radially expand automatically following deployment within the body. From the methods described hereinafter, methods employing balloon expansion techniques for introducing and assembling a multifurcated endovascular prosthesis in which the expandable support member and anchoring means does not expand automatically will be readily apparent to one skilled in the art.

In the method of the present invention, the aortic component 12 is first deployed within the aorta using a delivery system. The delivery system deploys the aortic component from a collapsed condition, in which the circumference of the aortic component is minimized so the aortic component can be delivered to the site of the abdominal aortic aneurysm intraluminally, to an expanded condition in which the circumference of the aortic component approaches a predetermined maximum circumference. As will be described more fully below, the aortic component is normally held in the collapsed condition by the delivery system during intraluminal delivery of the aortic component. Once properly located, the aortic component is deployed from the delivery system and radially expanded until its circumference firmly contacts the wall of the aorta.

FIG. 15 illustrates one embodiment of the delivery system for deploying the aortic component 12 in accordance with the present invention. The delivery system 300 comprises a cartridge sheath 302, a nosecone 304, and a pusher rod 306. The cartridge sheath 302 has a proximal end 308, a distal end 310, and a tubular wall 312 that extends along central axis 313 between the proximal end 308 and the distal end 310. The tubular wall 312 is formed from a conventional polymer, which is sufficiently flexible that it will readily bend as the cartridge sheath 302 is fed through the patient's vasculature during the intraluminal surgical procedure. The tubular wall 312 is preferably formed from a thin walled biocompatible polymer, having a thickness of about 0.003 to about 0.010 inches. Examples of biocompatible polymers that can be used to form the tubular wall 312 are polytetrafluoroethylene, nylon, TEFLON, and polyethylene. To add column strength or kink resistance, the wall 312 of the cartridge sheath 302 may include reinforcing, for example, stainless steel or fiber braiding.

The outer diameter of the cartridge sheath 302 is that diameter, which is sufficient to allow the cartridge sheath to be inserted through the patient's vasculature during the intraluminal surgical procedure. The inner diameter of the cartridge sheath 302 is about 12 to about 18 French.

Referring to FIGS. 15 and 16, the tubular wall 312 of the cartridge sheath 302 includes an inner surface 314. The inner surface 314 defines an inner lumen 316 that extends along the central axis 313 between a distal open end 318 in the distal end 310 of the cartridge sheath 302 and a proximal open end 319 in the proximal end 308 of the cartridge sheath 302. The lumen 316 is sized to receive and contain the aortic component 12 in a collapsed condition.

The distal end 310 may include radiomarkers (not shown) for readily identifying and locating the cartridge sheath under fluoroscopy. The radiomarkers may take the form of an annular ring formed from a metal, such as stainless steel, gold, or platinum, or from a radioopaque polymer. Referring to FIG. 15, the proximal end 308 of the cartridge sheath 302 may include any number of conventional accessories such as a hemostasis valve 320 to minimize backbleeding during insertion of the cartridge sheath 302 into the vasculature.

Referring to FIGS. 16 and 17, the wall 312 of the cartridge sheath 302 also includes a monorail lumen 322 that extends through the wall 312 of the cartridge sheath 302 along an outer axis 323, which is substantially parallel to the central axis 313. The monorail lumen 322 is radially spaced from the lumen 316 of the cartridge sheath so that the monorail lumen 322 extends adjacent the outer periphery of the cartridge sheath 302 substantially the length of the cartridge sheath 302. The diameter of the monorail lumen 322 is sized to allow the threading of a guide wire 370 through the monorail lumen 322. The monorail lumen 322 preferably has a diameter of about 0.040 inches (1.02 mm).

The cartridge sheath 302 is capped with the nosecone 304. The nosecone 304 is formed from a biocompatible material, such as polyurethane, TEFLON, polytetrafluoroethylene, polyethylene, or nylon.

The nosecone 304 preferably has an outer diameter, which is larger than the diameter of the opening 318 of the cartridge sheath 302 so that the nosecone 304 cannot be drawn into the cartridge sheath 302 as the cartridge sheath 302 and the nosecone 304 are moved relative to each other. The nosecone 304 has a first end 326 with a frustoconical or tapered shape adapted to facilitate advancement of the nosecone 304 through the patient's vasculature. The nosecone 304 has a second end 330 sized to fit against the opening 318 of cartridge sheath 302 so as to axially align the nosecone 304 with the cartridge sheath 302 in mated condition and seal the opening 318 of the cartridge sheath 302.

The nosecone 304 is connected to an elongated shaft 324, such as a stiff wire or hypodermic tubing, that extends through the lumen 316 of the cartridge sheath 302. The shaft 324 is slidable within the lumen 316 of the cartridge sheath 332 for longitudinal movement of the shaft and the nosecone 302 relative to the cartridge sheath 302.

The nosecone 304 includes a guide wire lumen 332 that extends longitudinally from a first opening 334 in the first end 326 of the nosecone 304 to a second opening 336 in the second end 330 of the nosecone 304. The first opening 334 of the guide wire lumen 332 is at a tip 328 of the first end 326, while the second opening 336 of the guide wire lumen 332 is at a point on the second end 330, which is coaxial with the monorail lumen 322 of the cartridge sheath 302 when the second end 330 of the nosecone 304 is mated to the cartridge sheath 302. The guide wire lumen 322 of the nosecone 304 communicates with the monorail lumen 322 of the cartridge sheath 302 to enable the guide wire 370 to be threaded through the nosecone 304 and into the guide wire lumen 332 of the cartridge sheath 302. The diameter of the guide wire lumen 332 of the nosecone 304 is, preferably, essentially the same as the diameter of the monorail lumen 322 of the cartridge sheath 302, and more preferably about 0.040 inches.

The pusher rod 306 can be co-axially disposed within the lumen 316 of the cartridge sheath 302 for slidable longitudinal movement with respect to the cartridge sheath 302 and the shaft 324. The pusher rod 306 is formed from a biocompatible material including polymers such as polyurethane, TEFLON, polytetrafluorethylene, or nylon, or metals such as stainless steel. The pusher rod 306 includes a distal end 340, which is sized to engage the collapsed aortic component 12 of the endovascular prosthesis 10 within the cartridge sheath 302 and urge the collapsed aortic component 12 of the endovascular prosthesis 10 from the cartridge sheath 302. The pusher rod 306 can also include a lumen 342 that extends coaxial with the central axis 313 the length of the pusher rod 306.

Referring to FIG. 18, the aortic component 12 is loaded into the delivery system 300 by first threading the nosecone 304 and the shaft 324 through the branch 64, the trunk portion 16, and the bare stent 20 of the aortic component 12 so that the nosecone 304 extends just beyond the bare stent of the aortic component. Fine metallic guide wires 350 are threaded through the branches 64 of the aortic component 12 so that one fine metallic wire extends from each branch. The fine metallic guide wires 350, as will described below, facilitate cannulation of the outflow limbs 14 during placement of the outflow limbs. The fine metallic guide wires 350 have a diameter of about 0.014 to about 0.018 inches.

Fine sutures 352 may then attached to each of the branches 64 of the aortic component 12 so that at least one fine suture 352 extends from each branch. The fine sutures 352 preferably comprise a high strength flexible yarn or monofilament of material, such as polyester, nylon, or wire. The fine sutures 352, as will be described in more detail below, can be used to provide traction to recapture the aortic component 12 when the aortic component 12 is at least partially deployed from the cartridge sheath.

Each suture 352 can be attached to a respective branch 64 of the aortic component 12 by looping each suture 352 through an eyelet 354 in the respective branch. As shown in FIG. 18, each eylet can be positioned so that each eyelet extends just through the inner and outer graft layer of each branch optionally, each eyelet can be positioned so that each eyelet extends through the rod and inner and outer graft layer of each branch. Although FIG. 18 shows separate fine sutures extending, respectively, from the eyelets (FIG. 18) of each branch, it is contemplated that a single fine suture (not shown) could be looped through all the eyelets of FIG. 18.

Alternatively, as shown in FIG. 19, a single suture 352 (or multiple fine sutures) can be attached to the branches 64(*a–d*) by looping the single suture 352 through sutures 356 that are connected to the open end 76 of each branch 64(*a–d*).

The aortic component 12 is then preferably cooled and radially compressed about the shaft 324. As illustrated in FIG. 20, the distal end 310 of the cartridge sheath 302 is then pulled over the aortic component 12, the fine wires 350, the fine sutures 352, and the shaft 324 so that the aortic component 12 is radially restrained within the lumen 316 of the cartridge sheath 302 and the distal end 310 of the cartridge sheath 302 engages the second end 330 of the nosecone 304. The second opening 336 in the nosecone 304 is then co-axially aligned with the monorail lumen 322 of the cartridge sheath 302 so that they communicate with each other. The pusher rod (not shown) is advanced through the lumen 316 of the cartridge sheath 302 until the distal end of the pusher rod engages the aortic component 12. The fine wires 350 and the fine suture(s) 352 are extended through the lumen 342 of the pusher rod and out a proximal end (not shown) of the pusher rod 306.

FIGS. 21A–21D illustrate a method of deploying the aortic component 12 using the delivery system 300 of the present invention. In the method, the femoral artery of the right leg of the patient to be treated is accessed percutaneously or by performing an arteriotomy. Using conventional fluoroscopic guidance techniques, a first guide wire 370 is introduced into the right femoral artery. FIG. 21A shows that the first guide wire 370 is advanced through the right (ipsilateral) external iliac artery (REIA) and the aorta (A) until a distal end of the guide wire is well above (i.e., superior) the abdominal aortic aneurysm (i.e., the guide wire is advanced past the renal arteries (RA) within the aorta).

Although the aorta is described in this embodiment as being accessed through the right femoral artery and the right (ipsilateral) external iliac artery (REIA), the aorta may potentially be accessed through the left femoral artery and the left (contralateral) external iliac artery.

The first guide wire 370 is at least about 0.025 inches in diameter, and preferably is about 0.035 inches to about 0.038 inches, and has a length of approximately 2 meters. The first guide wire 370 may be made of stainless steel that is covered with a synthetic material, such as TEFLON.

A proximal end (not shown) of the first guide wire 370 is then threaded through the guide wire lumen 332 of the nosecone 304 and through the monorail lumen 322 of the cartridge sheath 302. FIG. 21B shows that the nosecone 304 and the cartridge sheath 302, which contains the aortic component 12 in a collapsed condition within the lumen 316 of the cartridge sheath, is advanced over the guide wire 370 through the right femoral artery, the right (ipsilateral) external iliac artery (REIA) and the aorta until the distal end 310 of the cartridge sheath 302 extends just beyond the junction of the renal arteries (RA). Proper placement may be facilitated by use of the radiomarkers (not shown) on the distal end 310 of the cartridge sheath 302.

Figure 21C:
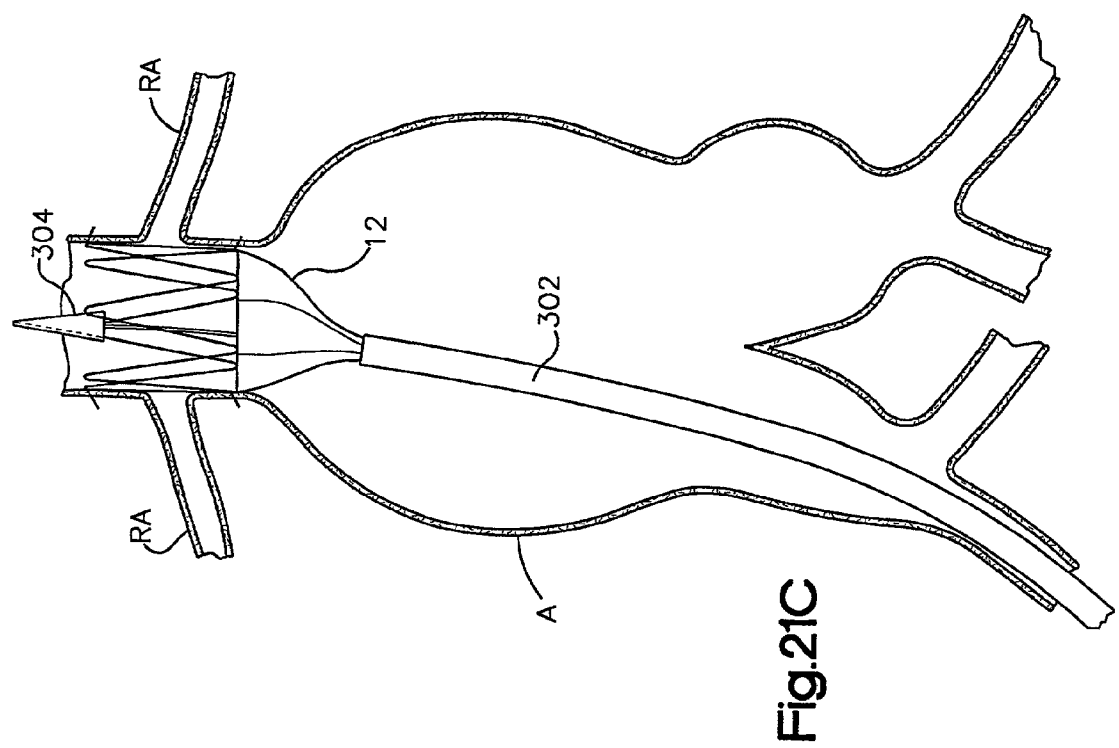

FIG. 21C shows that, once the distal end 310 of the cartridge sheath 302 is positioned just beyond the renal artery (RA) junction, the guide wire 370 is withdrawn through the nosecone 304 and cartridge sheath 302. Then, while maintaining the distal portion of the pusher rod in a fixed position, the cartridge sheath 302 is gradually withdrawn until the aortic component 12 is no longer contained by the cartridge sheath. With the cartridge sheath 302 no longer retaining the aortic component in a collapsed condition, the bare stent 20 and the expandable support member (not shown) of the aortic component will radially expand. Radial expansion of the bare stent 20 and the expandable support member will continue until the bare stent firmly engages the vascular wall of the aorta at the renal junction and the expandable support member radially expands the trunk portion 16 of the aortic component 12 to its maximum diameter.

The aortic component 12 can be repositioned, if necessary, prior to the bare stent 20 and the expandable support member 54 expanding to their maximum diameter, by first providing proximal traction to the fine suture(s) 352 that extend through the lumen 342 of the pusher rod 306. Proximal traction of the fine suture(s) 352 maintains the aortic component 12 in a fixed position relative to the pusher rod and the cartridge sheath so that the aortic component can be repositioned.

While the proximal traction of the fine suture(s) 352 is maintained, the cartridge sheath 302 can also be advanced distally over the aortic component. By advancing the cartridge sheath over the aortic component, the aortic component can be recaptured within the cartridge sheath and deployed, if necessary, at another location within the aorta or withdrawn from the patient.

After the aortic component 12 is deployed within the aorta, the fine suture(s) 352 are removed from the branches 64 of the aortic component 12 by gently pulling one end of each of the fine suture(s). The nosecone 304 and the shaft 324 are next withdrawn through the aortic component 12. The cartridge sheath 302, the nosecone 304, and the pusher rod 306 are then withdrawn through the aorta (A), the right (ipsilateral) external iliac artery (REIA), and the right femoral artery. FIG. 21D shows that only the deployed aortic component 12 and the fine wires 350, which extend from the right femoral artery through the branches 64 of the aortic component 12, remain in the patient's vasculature. The fine wires 350, as will be described below, are then used to deploy the outflow limbs 14(*a–d*).

FIGS. 22–24 illustrate a second embodiment of the delivery system for deploying the aortic component in accordance with the present invention. Referring to FIG. 22, the delivery system 500 comprises a cartridge sheath 502, a nosecone 504, and a pusher rod 506. The cartridge sheath 502 includes a proximal end 508, a distal end 510, and a tubular wall 512 that extends between the proximal end 508 and the distal end 510. The tubular wall 512 is formed from a conventional polymer, which is sufficiently flexible that it will readily bend as the cartridge sheath 502 is fed through the patient's vasculature during the intraluminal surgical procedure. The tubular wall 512 is preferably formed from a thin walled biocompatible polymer, having a thickness of about 0.003 to about 0.010 inches. Examples of biocompatible polymers that can be used to form the tubular wall 512 are polytetrafluorethylene, nylon, TEFLON, and polyethylene. To add column strength or kink resistance, the wall 512 of the cartridge sheath 502 may include reinforcing, for example, stainless steel or fiber braiding.

The outer diameter of the cartridge sheath 502 is that diameter, which is sufficient to allow the cartridge sheath to be inserted through the patient's vasculature during the intraluminal surgical procedure. The inner diameter of the cartridge sheath 502 is about 12 to about 18 French.

The wall 512 of the cartridge sheath 502 includes an inner surface 514 that extends between the distal end 510 and the proximal end 508 of the cartridge sheath 514. The inner surface 514 defines a cavity 516 that is sized to contain the aortic component 12 in the collapsed condition. The distal end 510 of the cartridge sheath 502 defines an opening 518 in the cartridge sheath 502. The distal end 510 may include radiomarkers (not shown) for readily identifying and locating the cartridge sheath 502 under fluoroscopy. The proximal end 508 of the cartridge sheath 502 may include any number of conventional accessories, such as a hemostasis valve 520 to minimize backbleed during insertion of the cartridge sheath into the patient's vasculature.

Referring to FIG. 23, the cartridge sheath 502 is capped with the nosecone 504. The nosecone 504 is formed from a biocompatible material such as polyurethane, TEFLON, polytetrafluoroethylene, or nylon. The nosecone 504 is connected to an elongated shaft 522, such as a stiff wire or hypodermic tubing, that extends through the cartridge sheath 502. The elongated shaft 522 is slidable within the cartridge sheath 502 for longitudinal movement of the shaft 522 and the nosecone 504 relative to the cartridge sheath 502.

The nosecone 504 preferably has an outer diameter which is larger than the diameter of the opening 518 of the cartridge sheath 502 so that the nosecone 504 cannot be drawn through the cartridge sheath 502 as the cartridge sheath 502 and the nosecone 504 are moved relative to each other. The nosecone 504 has a first end 524 with a frustoconical or tapered shape adapted to facilitate advancement of the nosecone 504 through the patient's vasculature. The nosecone 504 also has a second end 526 sized to fit against the opening 518 of the cartridge sheath 502 so as to axially align nosecone 504 with the cartridge sheath 502 in mated condition and seal the opening 518 of the distal end 510 of the cartridge sheath 502.

Referring to FIG. 24, the pusher rod 506 can be co-axially disposed within the cartridge sheath 502 for slidable longitudinal movement with respect to the cartridge sheath 502 and the shaft 522. The pusher rod 506 is formed from a biocompatible material including polymers such as polyurethane, TEFLON, polytetrafluoroethylene, or nylon, or metals such as stainless steel. The pusher rod 506 includes a distal end 528, which is sized to engage the collapsed aortic component 12 within the cartridge sheath 502 and urge the collapsed aortic component 12 from the cartridge sheath. The pusher rod 506 can also include a lumen 530 that extends the length of the pusher rod 506.

FIGS. 25 and 26A–26B illustrate a method of deploying the aortic component using the delivery system 500 in accordance with the second embodiment of the present invention. The nosecone 504 and the shaft 522 are threaded through the aortic component 504 so that the nosecone extends just beyond the bare stent 20 of the aortic component 12. Fine metallic guide wires 350 are threaded through the branches 64 of the aortic component 12 so that one fine metallic wire 350 extends from each branch. Fine sutures 352 are attached to each of the branches 64 of the aortic component 12 so that at least one fine suture extends from each branch of the aortic component 12. Alternatively, a single fine suture (not shown) could be attached to all of the branches so that only one fine suture extends from the aortic component.

The aortic component 12 is then preferably cooled and radially compressed about the shaft. Referring to FIG. 25, the distal end 510 of the cartridge sheath 502 is pulled over the aortic component 12, the fine wires 350, the fine sutures 352, and the shaft so that the aortic component 12 is radially restrained within the cavity 516 of the cartridge sheath and the distal end 510 of the cartridge sheath 50 engages the second end 526 of the nosecone 504. The pusher rod (not shown) is advanced through the lumen of the cartridge sheath until the distal end of the pusher rod engages the aortic component. The fine wires 350 and fine sutures 352 are extended through the lumen of the pusher rod and out a proximal end (not shown) of the pusher rod.

The femoral artery of the right leg (or left leg) of the patient to be treated is then accessed percutaneously or by performing an arteriotomy. Under conventional fluoroscopic guidance techniques, the cartridge sheath 502, capped with the nosecone 504 and containing the aortic component 12 is introduced in the right femoral artery (not shown), through the right (ipsilateral) external iliac artery, and into the aorta. FIG. 26A shows that the cartridge sheath 502 and nosecone 504 are advanced through the aorta until the distal end 510 of the cartridge sheath is just above (i.e., superior) the renal artery (RA) junction. Proper placement may be facilitated by use of the radiomarkers on the distal end of the aortic component.

Although the aorta is described in this embodiment as being accessed through the right femoral artery and the right (ipsilateral) external iliac artery (REIA), the aorta may potentially be accessed through the left femoral artery and the left (contralateral) external iliac artery.

Once the distal end 510 of the cartridge sheath 502 is positioned just beyond the renal artery (RA) junction, the cartridge sheath 502 is gradually withdrawn until the aortic component 12 is no longer covered by the cartridge sheath. With the cartridge sheath 502 no longer retaining the aortic component in a collapsed condition, the bare stent 20 and the expandable support member (not shown) of the aortic component will radially expand. FIG. 34B shows that radial expansion of the bare stent 20 and the expandable support member will continue until the bare stent firmly engages the wall of the aorta at the renal junction and the expandable support member radially expands the trunk portion 16 of the aortic component 12 to its maximum diameter.

The aortic component 12 can be repositioned, if necessary, prior to the bare stent 20 and the expandable support member expanding to their maximum diameter by first providing proximal traction to the fine suture(s) 352 that extend through the cartridge sheath 502. Proximal traction of the fine suture(s) 352 maintains the aortic component 12 in a fixed position relative to the pusher rod and the cartridge sheath so that the aortic component can be repositioned.

While the proximal traction of the fine suture(s) is maintained, the cartridge sheath 502 can also be advanced distally over the aortic component 12. By advancing the cartridge sheath over the aortic component, the aortic component can be recaptured within the cartridge sheath and deployed, if necessary, at another location within the aorta or withdrawn from the patient.

After the aortic component 12 is deployed within the aorta, the fine suture(s) 352 are removed from the branches 64 of the aortic component 12 by gently pulling one end of each fine suture(s) 352. The nosecone 540 and shaft 522 are next withdrawn through the aortic component 12. The cartridge sheath 502, the nosecone 504, the shaft 522, and the pusher rod 506 are then withdrawn through the aorta, right (ipsilateral) external iliac artery, and right femoral artery. Only the deployed aortic component 12 and the fine metallic guide wires 350, which extend from the right femoral artery through the branches 64 of the aortic component, remain in the patient's vasculature.

Figure 27B:
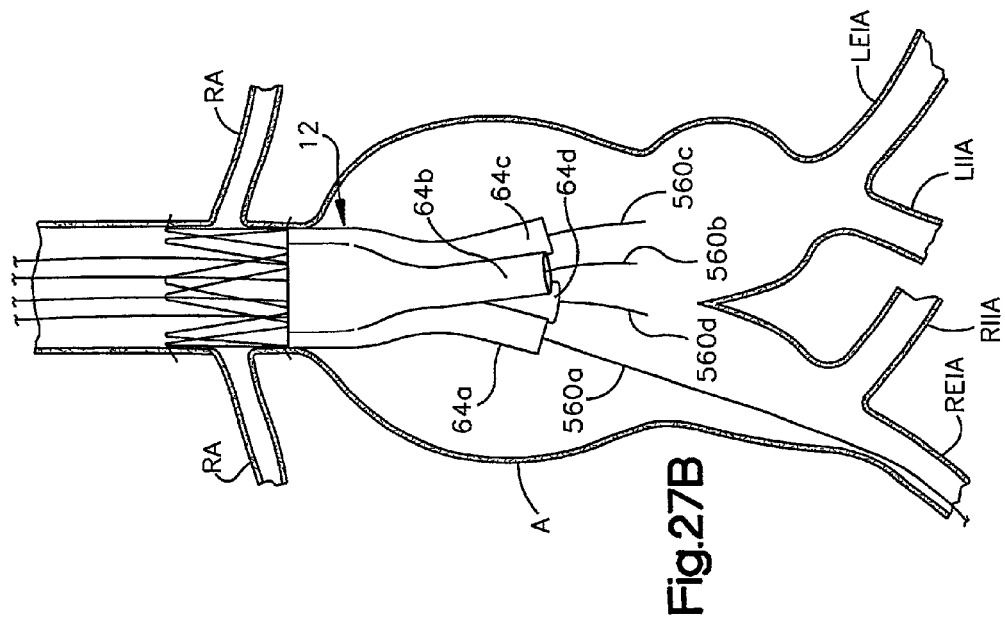
Figure 27A:
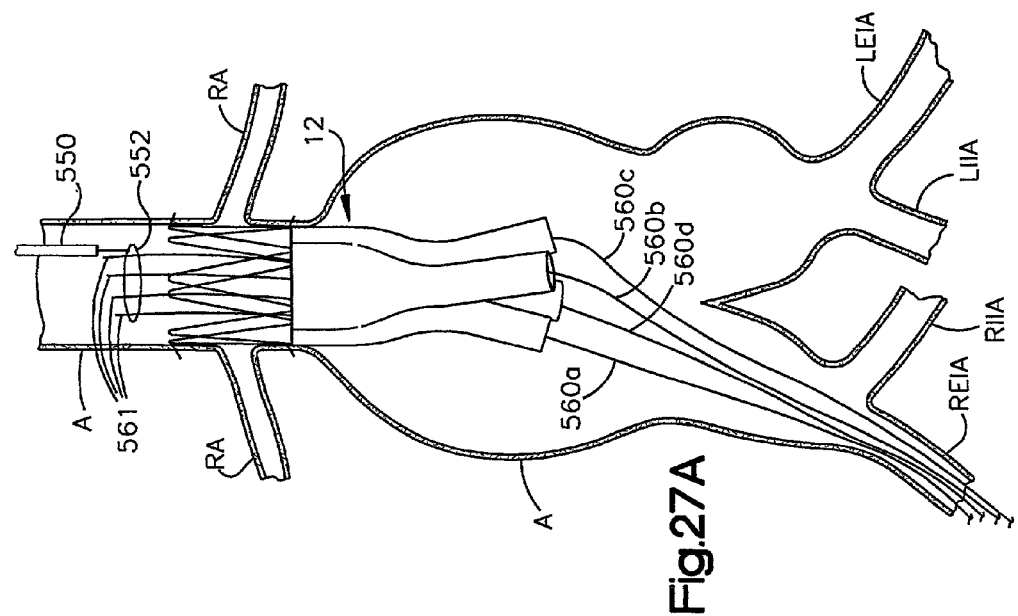

Following deployment of the aortic component 12 using the delivery system, fine catheters (not shown) are threaded through the right femoral artery over each of the fine wires 350. The fine wires 350 are withdrawn through the fine catheters and replaced with larger caliber guide wires 560 (a–d), (i.e., guide wires with an outer diameter of about 0.035 inches) (FIGS. 27A–27C). The guide wires 560(a–d) are then placed in separate outflow vessels so that each guide wire extends from a separate branch artery of the aorta (i.e., the right (ipsilateral) external iliac artery (REIA), right (ipsilateral) internal iliac artery (RIIA), left (contralateral) external iliac artery LEIA), and left (contralateral) internal iliac artery (LIIA)) to a separate branch 64 of the aortic component 12.

Referring to FIGS. 27A–27C, the guide wires 560(a–d) can be placed into the separate branches by first accessing the brachial artery (not shown) of the left arm (or right arm) of the patient being treated. The brachial artery can be accessed percutaneously or by performing an arteriotomy. A snare instrument 550 is introduced into the brachial artery at the point of the arteriotomy. The snare instrument 550 can be any well-known snare instrument, which is used during intraluminal surgery for capturing an item within the patient's vasculature. The snare instrument 550 is advanced through the left brachial artery and the aorta (A) until a snare 552 of the snare instrument is positioned just above (i.e., superior) the renal arteries (RA). Preferably, the snare 552 is opened until the diameter of the snare is substantially equal to the diameter of the aorta. FIG. 27A shows that the distal ends 561 of the guide wires 560(a–d) are then advanced through the aortic component 12 and the snare. The snare 552 is tightened around the distal ends 561 of the guide wires 560 and the guide wires 560 are withdrawn through the aorta (A) and left brachial artery.

Three of the guide wires 560(b–d) are then withdrawn through the brachial artery until the proximal ends of each of the three guide wires are positioned in the aorta just below (i.e., inferior) the branches of the aortic component. FIG. 27B shows that one guide wire 560a extends from the right (ipsilateral) external iliac artery, through the branch 64a of the aortic component 12 and the left brachial artery (not shown), while the three other guide wires 560(b–d) extend from the aorta, through the branches 64(b–d) of the aortic component 12 and the left brachial artery.

Referring to FIG. 27C, the three other guide wires 560 (b–d) are then advanced, respectively, into the right (ipsilateral) internal iliac artery (RIIA), the left (contralateral) internal iliac artery (LIIA), and the left (contralateral) external iliac artery (LEIA) using conventional fluoroscopic techniques so that each of the guide wires 560(a–d) extends from a separate branch artery to a separate branch 64(a–d) of the aortic component 12.

In an alternative embodiment of the present invention, one of the guide wires 560(a–d) can be placed in the left (contralateral) external iliac artery (LEIA) by capturing the guide wire with a surgical snare instrument that is extended through the left (contralateral) external iliac artery.

FIG. 28 illustrates a preferred embodiment of the surgical snare instrument 600 that can be used to capture one of the guide wires 560. The surgical snare instrument 600 includes an elongated tubular member 602 with a proximal end 604 and a distal end 606. The elongated tubular member 602 comprises a radio opaque tube that is made from a commercially available plastic material, such as medical grade nylon. The elongated tubular member 602 has an outer diameter of about 0.054 inches to about 0.066 inches and an inner diameter of about 0.036 inches to about 0.042 inches. The elongated tubular member 602 can be advanced through the patient's vasculature without permanent deformation.

Referring to FIG. 29, a control wire 608 with a proximal end 608 and a distal end 612 (FIG. 28) extends through the elongated tubular member 602. The control wire 610 is formed from a stainless steel wire with a diameter of about 0.018 inches to about 0.033 inches. The control wire 608 is slidable within the elongated tubular member 602 for longitudinal movement with the assistance of a handle 614 (FIG. 28).

The handle 614 includes a thumb piece 616 and a finger piece 618. The thumb piece 616 is connected to a side port connector 620, which is in turn connected to the elongated tubular member 602. The finger piece 618 is connected to a shaft 622, which is in turn connected to the proximal end 610 of the control wire 608. The finger piece 618 is slidable for longitudinal movement with respect to the thumb piece 616.

The distal end of the control wire 612 is connected to a snare wire 630. The snare wire 630 is formed from a stainless steel wire with a diameter of about 0.018 inches to about 0.033 inches. It should be noted, however, that the control wire 612 itself can form the snare wire 630.

The snare wire 630 forms a wire loop 632 that can be extended from the distal end 606 of elongated tubular member or be withdrawn within the elongated tubular member 602 by advancing or retracting the control wire 608. The control wire 608 is advanced or retracted by advancing or retracting the finger piece 618 relative to the thumb piece 616.

FIG. 30 shows that the wire loop 632 elastically expands to an open configuration when the wire loop 632 is extended from the distal end 606 of the elongated tubular member 602. The wire loop 632 in its open configuration has a substantially cardiodal shape with a first curved portion 634, a second curved portion 636, and cusp portion 638. The first curved portion 634 and the second curved portion 636 intersect to form the cusp portion 638 of the wire loop 632. Preferably, the wire loop 632 in an open configuration has a shape substantially similar to the shape illustrated in FIG. 30.

FIG. 31 shows that when the snare wire 630 is withdrawn within the elongated tubular member 602 the wire loop 632 elastically deforms and constricts the opening formed by the wire loop 632. The opening and constriction of the wire loop 632 allows the surgical snare instrument 600 to capture items inserted within the wire loop 632.

FIGS. 32A–32C illustrate the method in which the surgical snare instrument is used to capture a proximal end of one guide wire 560. In the method, the left (contralateral) femoral artery is accessed percutaneously or by performing an arteriotomy. The distal end 606 of the surgical snare instrument 600 is introduced into the left (contralateral)

femoral artery at the point of the incision and advanced through the left (contralateral) external iliac artery and into the aorta until the distal end 606 of the elongated tubular member 602 is just above (i.e., superior) the common iliac artery junction (CIAJ) within the aorta (A). The snare wire 630 is then extended from the distal end 606 of the elongated tubular member 602 to allow the wire loop 632 to elastically expand to its open configuration.

FIG. 32A shows that the wire loop 632 once extended from the distal end 606 of the elongated member 602 is positioned over the right (ipsilateral) common iliac artery. The wire loop 632 is maneuvered so that the cusp portion 638 of the wire loop 632 collects the guide wires 560(a–d) and positions the guide wires 560(a–d) away from the common iliac artery junction (CIAJ).

FIG. 32B shows that the proximal end 660 of one of the guide wires 560c is then inserted through the right (ipsilateral) femoral artery, right (ipsilateral) external iliac artery, and the wire loop 632 of the surgical snare instrument 602 while the distal end (not shown) of the guide wire 560c is maintained within the branch 64c of the aortic component 12.

The snare wire 630 is then withdrawn within the elongated tubular member 602. This causes the wire loop 632 to constrict and constrain the proximal end 660 of the guide wire 560c. The constrained proximal end 660 of the guide wire 560c and the elongated tubular member 602 are withdrawn through the left (contralateral) external iliac artery and left (contralateral) femoral artery (not shown). FIG. 32C shows that one of the fine wires 356 now extends from the left (contralateral) external iliac artery to the branch 64c of the aortic component while the other fine wires 350 extend from the right (ipsilateral) external iliac artery (IEIA) to the branches 64(a–c) of the aortic component 12.

Optionally, the guide wire 560C may include a flexible joint (i.e., hinge) that facilitates bending of the proximal end 660 of the guide wire 560C relative to a main portion of the guide wire. FIG. 33 illustrates one example of a hinge 680 that can be used with the guide wire 560c. The hinge 680 comprises a portion of the guide wire 560c that is revolved about an axis 682, which is lateral to the length of the guide wire. The portion of the guide wire 560c that forms the hinge 680 is distal the proximal end 660 of the guide wire 560c.

FIG. 34a shows that the proximal end 660 of the guide wire 560 can be inserted through the wire loop 632 of the snare instrument 600 so that the hinge 680 is positioned within the wire loop. The wire loop 632 can then be constrained about the hinge 680 of the guide wire. FIG. 34b shows that the guide wire will bend at the hinge 680 allowing the guide wire 560c to be readily withdrawn into the elongated tubular member 602 of the snare instrument 600.

Once the guide wires 560(a–d) are placed in the branch arteries, the outflow limbs 14(a–d) are deployed using an outflow limb delivery system. The outflow limb delivery system used to deploy the outflow limbs is similar to the first embodiment of the aortic component delivery system used to deploy the aortic component except the dimensions of the components of outflow limb delivery system are sized to accommodate an outflow limb instead of the aortic component.

FIG. 35 illustrates an outflow limb delivery system 700 in accordance with the present invention. The outflow limb delivery system 700 includes a cartridge sheath 702, a nosecone 704, and a pusher rod 706. The cartridge sheath 702 includes a proximal end (not shown), a distal end 708 and a tubular wall 710 that extends along a central axis 711 between the proximal end and the distal end 708. The inner diameter of the cartridge sheath 702 of the outflow limb delivery system 700, unlike the cartridge sheath of the aortic component delivery system, is preferably about 8 to 14 French.

The wall 710 of the cartridge sheath 702 has an inner surface 712 that defines a lumen 714 which is sized to contain an outflow limb 14 in the collapsed condition. The distal end 708 of the cartridge sheath 702 defines an opening 716 in the cartridge sheath 702. The wall 710 of the cartridge sheath 702 also includes a monorail lumen 718 that extends through the wall 710 of the cartridge sheath 702 along an axis 719, which is substantially parallel to the central axis 711. The monorail lumen 718 is radially spaced from the lumen 714 of the cartridge sheath so that the monorail lumen 718 extends adjacent the outer periphery of the cartridge sheath 702 substantially the length of the cartridge sheath 702. The diameter of the monorail lumen 718 is sized to allow the threading of a guide wire through the monorail lumen 718. The monorail lumen preferably has a diameter of about 0.040 inches (1.02 mm).

The cartridge sheath can be capped with the nosecone 704. The nosecone 704 is connected to a shaft 720, such as a stiff wire or hypodermic tubing, which extends through the lumen 714 of the cartridge sheath 702. The shaft 720 is slidable within the lumen 714 of the cartridge sheath 702 for longitudinal movement of the shaft 720 and the nosecone 704 relative to the cartridge sheath 702.

The nosecone 704 preferably has an outer diameter, which is larger than the inner diameter of the cartridge sheath 702 so that the nosecone cannot be drawn through the cartridge sheath 702 as the cartridge sheath 702 and the nosecone are moved relative to each other. The nosecone 704 has a first end 722 with a frustoconical or tapered shape adapted to facilitate advancement of the delivery system 700 through the patient's vasculature. The nosecone has a second end 726 sized to fit against the opening 716 of cartridge sheath 702 so as to axially align nosecone 704 with the cartridge sheath 702 in mated condition and seal the opening 716 of the cartridge sheath 702.

The nosecone 704 includes a guide wire lumen 730 that extends longitudinally from a first opening 724 in the first end 722 of the nosecone to a second opening 734 in the second end 726 of the nosecone 704. The first opening 732 of the guide wire lumen 730 is at a tip 724 of the first end 722, while the second opening 734 of the guide wire lumen 730 is at a point on the second end 731, which is coaxial with the monorail lumen 718 of the cartridge sheath 702 when the second end 726 of the nosecone is mated to the cartridge sheath 702. The guide wire lumen 730 of the nosecone 704 communicates with the monorail lumen 718 of the cartridge sheath 702 to enable a guide wire (not shown) to be threaded through the nosecone 704 and into the monorail lumen 718 of the cartridge sheath 702. The diameter of the guide wire lumen 730 is preferably essentially the same as the diameter of the monorail lumen 718 of the cartridge sheath 702, and more preferably about 0.040 inches.

The pusher rod 706 can be co-axially disposed within the lumen 714 of the cartridge sheath 702 for slidable longitudinal movement with respect to the cartridge sheath 702 and the shaft 720. The pusher rod 706 includes a distal end 740 that is sized to engage a collapsed outflow limb 14 within the cartridge sheath 702 and urge the collapsed outflow limb from the lumen 714 of the cartridge sheath. The pusher rod 706 can also includes a lumen 742 that extends coaxial with the central axis 711 along the length of the pusher rod.

FIGS. 36 and 37A–37C illustrate a method of deploying the outflow limbs 14(a–d) using the delivery system 700 in accordance with the present invention. The outflow limb 14a is initially loaded in the lumen 714 of the cartridge sheath 702 by first threading the nosecone 704 and the shaft 720 through the outflow limb. The outflow limb 14a is then preferably cooled and radially compressed about the shaft 720.

FIG. 36 shows that the distal end 708 of the cartridge sheath 702 is pulled over the outflow limb 14a and the shaft 720 so that the outflow limb 14a is radially restrained within the lumen 714 of the cartridge sheath 702 and the distal end 708 of the cartridge sheath 702 engages the second end 726 of the nosecone 704. The guide wire lumen 730 of the nosecone 704 is co-axially aligned with the monorail lumen of the cartridge sheath so that they communicate with one another. A proximal end (not shown) of guide wire 560a is then threaded through the guide wire lumen 730 of the nosecone 704 and the monorail lumen 718 of the cartridge sheath 702. The pusher rod (not shown) is advanced through the lumen 714 of the cartridge sheath 702 until the distal end 708 of the pusher rod engages the outflow limb.

Figure 37A:
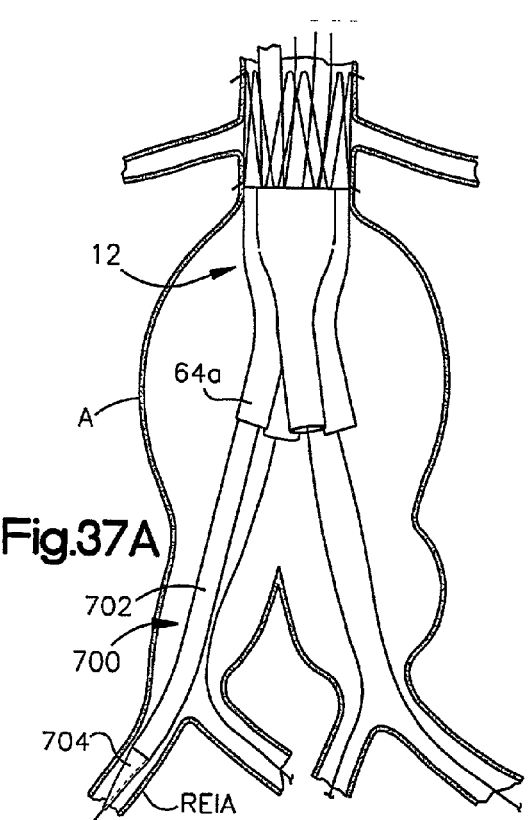
FIGS. 37a–37c illustrate a method of deploying the outflow limbs using the outflow limb delivery system in accordance with the present invention.
Figure 37B:
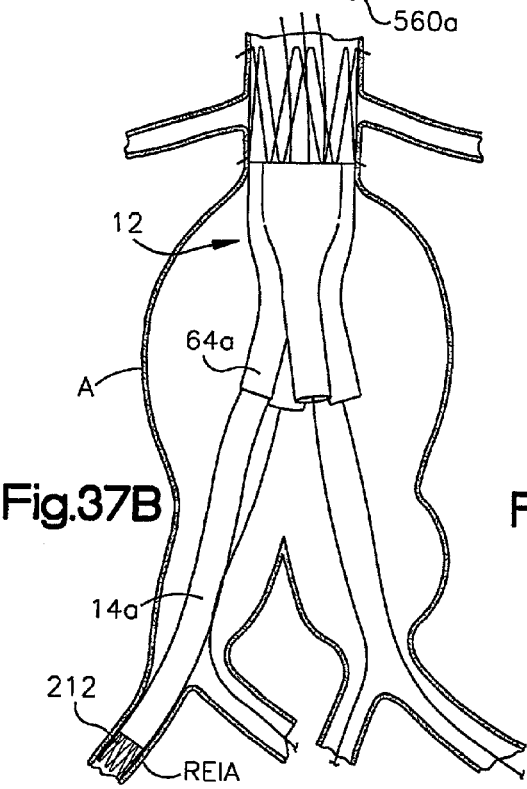

FIG. 37A shows that the nosecone 704 and the cartridge sheath 702, with the collapsed outflow limb 14a, is advanced over the guide wire 560a through the brachial artery (not shown) and the aortic component and into the right (ipsilateral) external iliac artery (REIA). Once the distal end 708 of the cartridge sheath 702 is positioned within the right (ipsilateral) external iliac artery (REIA), the guide wire 560a is withdrawn through the brachial artery. Then, while maintaining the distal end 740 of the pusher rod 706 in a fixed position, the cartridge sheath 702 is gradually withdrawn until the outflow limb 14a is no longer covered by the cartridge sheath 702. With the cartridge sheath 702 no longer retaining the outflow limb 14a in a collapsed condition, the bare stent 212 (shown in FIG. 37B) and the expandable support member 194 (not shown in FIGS. 37A–37C) of the outflow limb will radially expand as the temperature of the bare stent 212 and the expandable support member 194 increases. FIG. 37B shows that the radial expansion of the bare stent 212 and the expandable support member 194 will continue until the bare stent firmly engages the vascular wall of the right (ipsilateral) external iliac artery (REIA) and the first end of the outflow limb is firmly secured within the branch 64a of the aortic component 12.

Figure 37C:
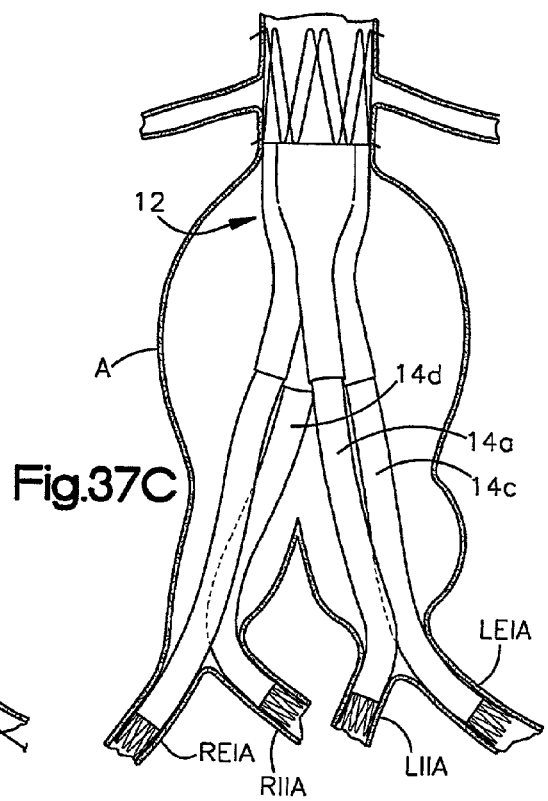

This method of deploying the outflow limb 14a by cannulating the compressed outflow limb using the outflow flow limb delivery system 700 is repeated until, as illustrated in FIG. 37C, the outflow limbs 14b, 14c, and 14d extend from the remaining branches of the aortic component to the right (ipsilateral) internal iliac artery, left (contralateral) internal iliac artery, and left (contralateral) external iliac artery.

FIG. 38 illustrates an alternative embodiment of a furcated endovascular prosthesis. The furcated endovascular prosthesis 800 in accordance with this embodiment includes an aortic component 802 with a trunk portion 804, a furcated portion 806, and an anchoring means 808. The trunk portion 804 and the anchoring means 808 are similar in construction to the trunk portion 16 and the anchoring means 20 of the aortic component 12 of the furcated endovascular prosthesis 10. The furcated portion 806 of the aortic component 802 is also similar in construction to the furcated portion 18 of the aortic component 12 of the furcated endovascular prosthesis 10, except that in the present embodiment the furcated portion 806 includes six branches 809 (instead of the four branches 64) that extend from an intersection (not shown) of the furcated portion 806.

The endovascular prosthesis 800 also includes six outflow limbs 810(a–f). The outflow limbs 810(a–f) have a construction similar to the construction of the outflow limbs 14(a–d) of the furcated endovascular prosthesis 10. The outflow limbs 810(a–f) each have a first end 812 that articulates with a branch 809 of the furcated portion 806 and a second end 814 that articulates with a branch artery of the aorta.

The furcated endovascular prosthesis 800 in accordance with this embodiment is used to treat a thoracoabdominal aneurysm that extends within the aorta from just below (i.e., inferior) the left subclavian artery (LSCA) to just above (i.e., superior) the common iliac artery junction (CIAJ). Accordingly, the aortic component 802 is deployed just below the left subclavian artery (LSCA) so that the anchoring means 808 overlaps the junction of the left subclavian artery junction (LSCA) and the aorta (A). The six outflow limbs 810(a–f) are deployed so that the first ends 812 of the outflow limbs articulate with a branch 809 of the furcated portion 806 and the second ends 814 of outflow limbs articulate, respectively, with that the celiac artery (CA), the superior mesenteric artery (SMA), the left renal artery (LRA), the right renal artery (LRA), the right common iliac artery (RCIA), and the left common iliac artery (LCIA).

FIGS. 39 and 40 illustrate a further embodiment of a furcated endovascular prosthesis. The furcated endovascular prosthesis 900 in accordance with this embodiment includes an aortic component 902 and four outflow limbs 904(a–d) that extend from the aortic component 902. The aortic component 902 includes a trunk portion 906 and a furcated portion 908. The trunk portion 906 and furcated portion 908 are similar in construction to the trunk portion 16 and the furcated portion 18 of the aortic component 12 of the furcated endovascular prosthesis 10. Although, the aortic component is illustrated as not including an anchoring means, an anchoring means may be provided to further secure the aortic component within the vasculature.

The outflow limbs 904(a–c) have a construction similar to the construction of the outflow limbs 14(a–d) (FIG. 1). The outflow limbs 904(a–c) each have a first end 912 that articulates with a branch of the furcated portion 908 and a second end 914 that articulates with an artery. The diameter of the outflow limbs can vary depending on the diameter of the respective branch and arteries they articulates with.

The furcated endovascular prosthesis may include a valve 916. The valve 916 is disposed within a trunk lumen 918 of the trunk portion 906. The valve 916 extends across (i.e., transverse) the trunk lumen 916 of the trunk portion 906. Although the valve 916 is illustrated as being disposed in the trunk portion 906 of the aortic component 902, the valve 916 could be disposed in other areas of the endovascular prosthesis 900. Alternatively, the furcated endovascular prosthesis may not include a valve.

Referring to FIG. 39, the valve 916 includes three leaflets 920(a–c) that radially extend from an inner annular surface 922 of the trunk portion 906. The leaflets 920(a–c) allow for one-way flow of blood through the endovascular prosthesis 900. The valve 916 could alternatively include two or more than three leaflets that allow for one-way flow of blood through the endovascular prosthesis 900.

The furcated endovascular prosthesis 900 in accordance with this embodiment is used to treat an ascending aneurysm that extends within an ascending portion of the aorta. Accordingly, the aortic component 902 is deployed within the aorta just above heart so that the furcated portion 908 extends up through the ascending aorta (AA). The four outflow limbs 904(*a–d*) are deployed so that the first ends 912 of the outflow limbs each articulate with a branch of the furcated portion 908 and the second ends 914 of the outflow limbs each articulate respectively with the brachiocephalic artery (BA), the common carotid artery (CCA), the left subclavian artery (LSCA) and the descending part of the aorta (DA).

From the above description of the invention, those skilled in the art will perceive improvements changes and modifications. Such improvements, changes and modifications within the skill of the art intended to be covered by the appended claims.

Having described the invention, we claim:

1. An endovascular prosthesis comprising:
    a trunk portion having a first end, a second end, and a trunk lumen extending between said first end and said second end of said trunk portion, said trunk portion including a radially expandable support, an inner layer of fabric which at least partially defines said trunk lumen, and an outer layer of fabric which at least partially defines an outer side of said trunk portion, said radially expandable support being at least partially disposed between said inner and outer layers of fabric;
    a furcated portion connected to said second end of said trunk portion, said furcated portion including a plurality of branches extending from said second end of said trunk portion and having branch lumens in fluid communication with said trunk lumen, said inner layer of fabric at least partially defines said branch lumens, said outer layer of fabric at least partially defines outer sides of said branches;
    said trunk portion is formed by a number of sections equal to the number of branches in said furcated portion, said sections of said trunk portion being interconnected by a plurality of continuous seams which are free of corners along their length and which interconnect said inner and outer layers of fabric, a first end of each of said seams being disposed on a central axis of said trunk portion at an intersection of said furcated portion, a second end of each of said seams being disposed at said first end of said trunk portion and spaced from the central axis of said trunk portion, each one of said seams having an arcuately curving portion which extends from the first end of said one seam into said trunk portion and a linear portion which extends from the arcuately curving portion of said one seam to the second end of said one seam, said inner and outer layers of fabric extend from said first end of said trunk portion to ends of said branches which are spaced furthest from said trunk portion; and
    a plurality of tubular outflow limbs each of which is telescopically connected with one of said branches, each of said outflow limbs extends from one of said branches and has a limb lumen in fluid communication with said trunk lumen, each of said outflow limbs having a radially expandable limb support, an inner layer of fabric which at least partially defines said limb lumen, and an outer layer of fabric which at least partially defines an outer side of said limb, said radially expandable limb support of each one of said outflow limbs being at least partially disposed between said inner and outer layers of fabric of said one outflow limb.

2. An endovascular prosthesis as set forth in claim 1 wherein each one of said branches includes a single linear rod which is disposed between said inner and outer layers of fabric which at least partially define said one branch.

3. An endovascular prosthesis as set forth in claim 1 wherein said inner and outer layers of fabric which at least partially define said trunk portion have uniaxially oriented fibril microstructures.

4. An endovascular prosthesis as set forth in claim 3 wherein each of said inner and outer layers of fabric which at least partially define said trunk portion have a thickness of about 0.1 mm.

5. An endovascular prosthesis as set forth in claim 4 wherein said inner and outer layers fabric which at least partially define said trunk portion are interconnected by sintering to form a substantially monolithic covering for at least a portion of said radially expandable support.

6. An endovascular prosthesis as set forth in claim 1 further including a stent extending from said first end of said trunk portion with at least a portion of said stent spaced from said inner and outer layers of fabric, said stent having surfaces which are adapted to engage an inner side surface of a first blood vessel at a location in an upstream blood flow direction of a junction between said first blood vessel and a second blood vessel, said stent extends downstream past the junction between said first and second blood vessels, said trunk portion being disposed in a downstream blood flow direction of the junction between said first and second blood vessels.

7. An endovascular prosthesis as set forth in claim 1 wherein said radially expandable support is spaced apart from said furcated portion.

8. An endovascular prosthesis as set forth in claim 1 wherein each one of said branches includes a rod which extends from a location adjacent to said intersection of said furcated portion to a location adjacent to an end of said one branch which is spaced from said intersection, said rod being disposed between said inner and outer layers of fabric.

9. An endovascular prosthesis as set forth in claim 1 wherein said inner and outer layers of fabric are bonded together.

10. An endovascular prosthesis as set forth in claim 1 wherein said inner layer of fabric is coextensive with said outer layer of fabric.

* * * * *